(12) United States Patent
Kim

(10) Patent No.: US 8,860,504 B2
(45) Date of Patent: Oct. 14, 2014

(54) METHOD AND APPARATUS FOR MEASURING BIOLOGICAL SIGNAL

(75) Inventor: Jong-pal Kim, Seoul (KR)

(73) Assignee: Samsung Electronics Co., Ltd. (KR)

( * ) Notice: Subject to any disclaimer, the term of this patent is extended or adjusted under 35 U.S.C. 154(b) by 145 days.

(21) Appl. No.: 13/031,958

(22) Filed: Feb. 22, 2011

(65) Prior Publication Data

US 2011/0237904 A1    Sep. 29, 2011

(30) Foreign Application Priority Data

Mar. 26, 2010  (KR) .................. 10-2010-0027547

(51) Int. Cl.
| | | |
|---|---|---|
| *H03B 1/00* | (2006.01) | |
| *A61B 5/00* | (2006.01) | |
| *A61B 5/0402* | (2006.01) | |
| *A61B 5/0408* | (2006.01) | |

(52) U.S. Cl.
CPC ............. *A61B 5/0402* (2013.01); *A61B 5/7207* (2013.01); *A61B 5/0408* (2013.01)
USPC ............................ 327/552; 600/301; 600/483

(58) Field of Classification Search
USPC ........... 327/552, 553, 558; 600/301, 481, 483
See application file for complete search history.

(56) References Cited

U.S. PATENT DOCUMENTS

| | | | | |
|---|---|---|---|---|
| 4,537,200 | A * | 8/1985 | Widrow ........................ | 600/509 |
| 6,208,888 | B1 | 3/2001 | Yonce | |
| 7,474,247 | B1 * | 1/2009 | Heinks et al. ................. | 341/155 |
| 7,706,495 | B2 * | 4/2010 | Hirano et al. ................. | 375/373 |
| 8,046,042 | B2 * | 10/2011 | Diab et al. ..................... | 600/336 |
| 8,162,844 | B2 * | 4/2012 | Carlson et al. ................ | 600/528 |
| 8,273,053 | B2 * | 9/2012 | Saltzstein .................. | 604/93.01 |
| 8,275,140 | B2 * | 9/2012 | Smith .............................. | 381/67 |

FOREIGN PATENT DOCUMENTS

| | | |
|---|---|---|
| JP | 2001-327476 A | 11/2001 |
| JP | 2008-284352 A | 11/2008 |
| KR | 1020060035654 A | 4/2006 |
| KR | 1020060054644 A | 5/2006 |
| KR | 10-0725580 B1 | 5/2007 |

* cited by examiner

*Primary Examiner* — Lincoln Donovan
*Assistant Examiner* — Jung H Kim
(74) *Attorney, Agent, or Firm* — Cantor Colburn LLP

(57) ABSTRACT

An apparatus for measuring a biological signal of a body, the apparatus including; at least three interfaces which obtain signals from the body, a signal application unit which applies a signal having a frequency which is higher than one of a frequency of interest of the biological signal to one of a first interface from among the at least three interfaces, and one of a plurality of internal elements of the apparatus, a feedback signal generation unit which generates a feedback signal from component signals generated due to the applied signal, wherein the feedback signal generation unit generates the feedback signal using a signal obtained from at least one of a second interface and a third interface from among the at least three interfaces and an input control unit which receives the generated feedback signal and controls a signal input from at least one of the second interface and third interface to an amplifier.

16 Claims, 17 Drawing Sheets

METHOD AND APPARATUS FOR MEASURING BIOLOGICAL SIGNAL

CROSS-REFERENCE TO RELATED APPLICATION

This application claims priority to Korean Patent Application No. 10-2010-0027547, filed on Mar. 26, 2010, and all the benefits accruing therefrom under 35 U.S.C. §119, the content of which in its entirety is herein incorporated by reference.

BACKGROUND

1. Field

The present disclosure relates to methods and apparatuses for measuring a biological signal.

2. Description of the Related Art

As interest in health-related issues increases, various methods have been developed to monitor a health status of an individual. Typically, such methods measure the biological signals of the individual's body. For example, an electrocardiogram ("ECG") test may be performed to check for heart diseases and high blood pressure. The ECG test may be performed by amplifying signals detected from interfaces, e.g., electrodes, attached on a subject, i.e., a person, and continuously monitoring the amplified signals.

SUMMARY

Provided are methods and apparatuses for measuring a biological signal from which noise is removed.

Provided are computer-readable recording media having recorded thereon a computer program for executing the methods.

Additional aspects will be set forth in part in the description which follows and, in part, will be apparent from the description, or may be learned by practice of the presented embodiments.

According to an aspect of the present disclosure, an apparatus for measuring a biological signal of a body includes; at least three interfaces which obtain signals from the body, a signal application unit for which applies a signal having a frequency which is higher than a frequency of interest of the biological signal to one of a first interface from among the at least three interfaces, and one of a plurality of internal elements of the apparatus, a feedback signal generation unit which generates a feedback signal from component signals generated due to the applied signal, wherein the feedback signal generation unit generates the feedback signal using a signal obtained from at least one of a second interface and a third interface from among the at least three interfaces, and an input control unit which receives the generated feedback signal and controls a signal input from at least one of the second interface and the third interface to an amplifier.

According to another aspect of the present disclosure, a method of measuring a biological signal of a body using an apparatus for measuring the biological signal includes; obtaining signals from the body by using at least three interfaces, applying a signal having a frequency higher than a frequency of interest of the biological signal to at least one of a first interface from among the at least three interfaces, and one of a plurality of internal elements of the apparatus, generating a feedback signal from component signals generated due to the applied signal using a signal obtained from at least one of a second interface and a third interface from among the at least three interfaces, receiving the generated feedback signal, controlling a signal input from at least one of the second interface and the third interface and sending the controlled signal to an amplifier; and outputting a measured biological signal of the body using the controlled signal.

According to another aspect of the present disclosure, a non-transitory computer readable recording medium has recorded thereon a computer program for executing the above-described method.

According to another aspect of the present disclosure, an apparatus for measuring a biological signal of a body includes; at least three interfaces which obtain signals from the body, a signal application unit which applies a carrier signal to at least one of a first interface from among the at least three interfaces, and one of a plurality of internal elements of the apparatus, and a feedback signal generation unit which generates a feedback signal from component signals generated due to the applied carrier signal using a signal obtained from at least one of a second interface and a third interface from among the at least three interfaces, wherein the carrier signal is synthesized based on a signal having a frequency higher than a frequency of interest of the biological signal, and the feedback signal received from the feedback signal generation unit, and is output from the signal application unit.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
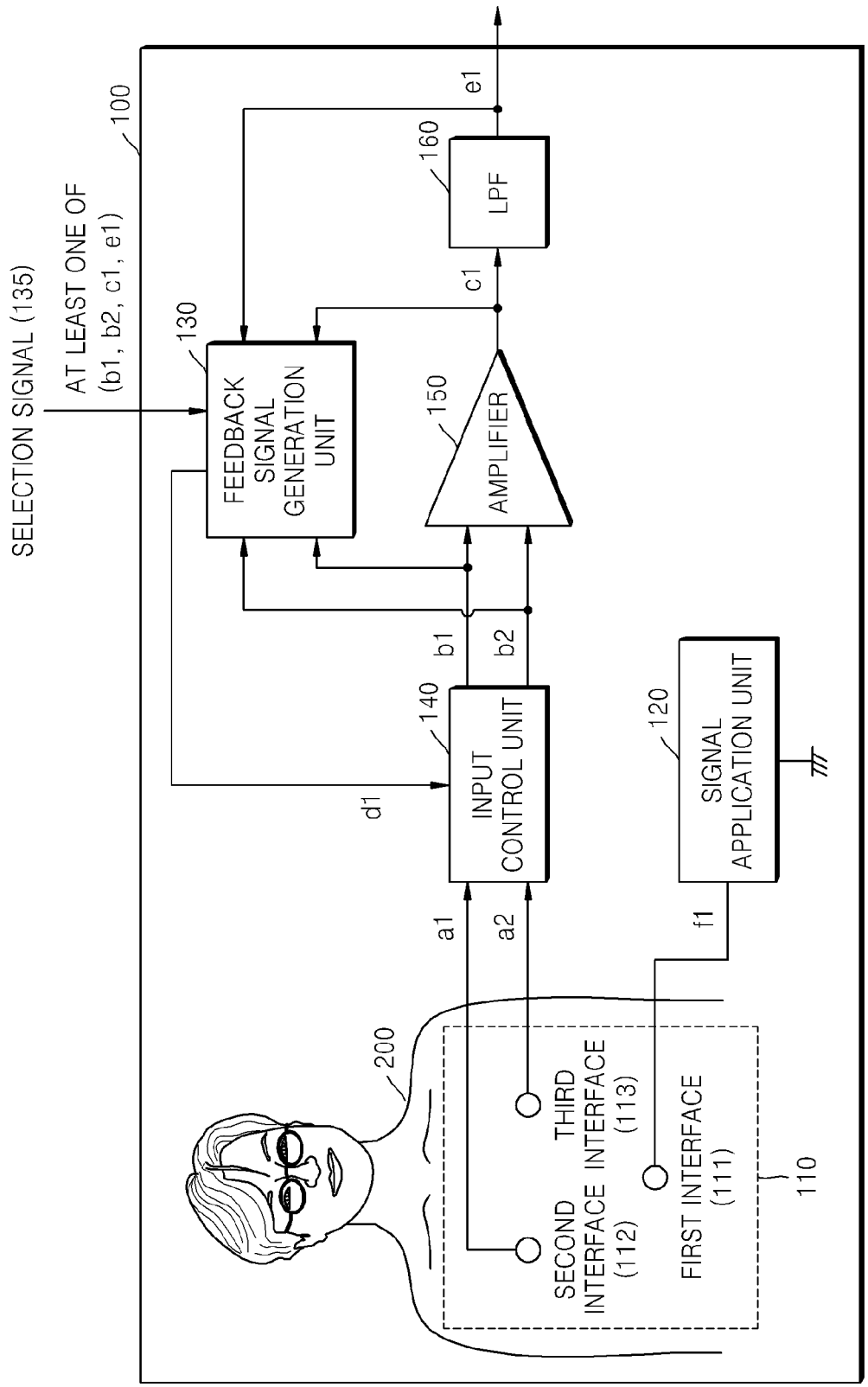
FIG. 1 is a structural view of an embodiment of an apparatus for measuring a biological signal according to the present disclosure.

Embodiments now will be described more fully hereinafter with reference to the accompanying drawings, in which embodiments are shown. These embodiments may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the disclosure.

All methods described herein can be performed in a suitable order unless otherwise indicated herein or otherwise clearly contradicted by context. The use of any and all examples, or exemplary language (e.g., "such as"), is intended merely to better illustrate the disclosure and does not pose a limitation on the scope thereof unless otherwise claimed. No language in the specification should be construed as indicating any non-claimed element as essential to the practice of the embodiments as used herein.

Hereinafter, the embodiments will be described in detail with reference to the accompanying drawings.

FIG. 1 is a structural view of an embodiment of an apparatus 100 for measuring a biological signal according to the present disclosure. Referring to FIG. 1, the apparatus 100 includes at least three interfaces 110, e.g., first through third interfaces 111 through 113, a signal application unit 120, a feedback signal generation unit 130, an input control unit 140, an amplifier 150 and a low pass filter ("LPF") 160.

Although only elements related to the current embodiment are illustrated in FIG. 1, it would be understood by one of ordinary skill in the art that the apparatus 100 may further include other general-use elements, in addition to the elements illustrated in FIG. 1.

The apparatus 100 measures a biological signal of a subject 200, i.e., a person, using signals obtained from the interfaces 110 that contact, or are adjacent to, different spots on the body of the subject 200. The apparatus 100 is a medical apparatus for measuring the biological signal of the subject 200. For example, the apparatus 100 may be an electroencephalograph, an electroencephalogram ("EEG") sensor, a retinal electrometer, a sphygmograph, a tocomonitor, a thermograph, a slit lamp microscope, an extensometer, a phonocardiograph, an electrocardiograph, a thermometer, a scale, a ultrasonic blood flow meter, a blood pressure meter, a blood glucose meter, a spirometer or other similar apparatus. Here, the biological signal may be an EEG signal, an electrocardiogram ("ECG") signal, an electromyogram ("EMG") signal, a body temperature, a blood pressure, a weight, a body mass index, a fat mass index, a liver function index, a cholesterol level, a blood sugar level, a heart rate, an oxygen saturation level or other similar measurements of the body of the user.

Hereinafter, the apparatus 100 will be described as measuring an ECG signal of the subject 200 for convenience of explanation. However, it would be understood by one of ordinary skill in the art that the biological signal may include values or indices, states and symptoms related to health, that the apparatus 100 may include all apparatuses and equipment for measuring the biological signal of the subject 200, and that a plurality of the above-mentioned biological signals may be simultaneously or sequentially measured using one apparatus.

The ECG signal refers to a curve for recording a current corresponding to the movement of heart muscles. That is, an action potential, which is generated when heart muscles of the subject 200 are contracted and relaxed, generates a current that spreads from the heart to every part of the body, and this current has potential differences according to positions within the body. These potential differences may be obtained by at least two of the interfaces 110 that are attached on, or adjacent to, the skin of the subject 200, and may represent the ECG signal of the body of the subject 200.

The interfaces 110 contact, or are adjacent to, the body of the subject 200, and obtain signals from the subject 200. Hereinafter, it is assumed for convenience of explanation that the interfaces 110 include the first through third interfaces 111 through 113. However, it would be understood by one of ordinary skill in the art that the number of the interfaces 110 is not limited to three and that alternative embodiments include configurations wherein four or more interfaces may be included.

Each of the first through third interfaces 111 through 113 may electrically interface with the body. For example, the biological signal from the body of the subject 200 may be measured using the first through third interfaces 111 through 113, which are electrodes.

In more detail, embodiments of the interfaces 110 that electrically interface with the body may include wet-type electrodes, dry-type electrodes, insulating-type electrodes, probe-type electrodes or other similar devices. A wet-type electrode interfaces with the skin using a gel-type material, a dry-type electrode interfaces with the skin using a solid-type conductive material such as metal, conductive fabric, or conductive rubber, an insulating-type electrode interfaces with the skin using capacitive coupling caused by an insulating material, and a probe-type electrode interfaces with the skin while penetrating through an outer layer of the skin.

In such an embodiment, the insulating-type electrode uses capacitive coupling and thus may electrically interface with the skin even while being adjacent to the skin and not contacting the skin. Also, when electrical interfaces interface with the body, the electrical interfaces may be individually separate from each other, or some or all of the electrical interfaces may be included as a single element.

The first through third interfaces 111 through 113 may contact or be adjacent to different spots of the body, and the locations of the spots may be variably chosen, such as a chest and a wrist.

The signal application unit 120 applies a signal having a frequency higher than a frequency of interest of the biological signal to the first interface 111 or one of the internal elements of the apparatus 100. That is, if the frequency of interest of the biological signal is 100 Hz, the signal application unit 120 applies a signal having a frequency greater than 100 Hz to the first interface 111 or one of the internal elements of the apparatus 100. The signal application unit 120 does this in order to maintain a voltage in the first interface 111, from among the interfaces 110, to have a frequency higher than a frequency of interest of the biological signal. In this regard, the apparatus 100 may eliminate noise signal efficiently.

In this case, the frequency of interest refers to a frequency band of the biological signal to be measured. For example, when the ECG signal is measured as the biological signal, the frequency of interest of the ECG signal refers to a frequency band of the ECG signal of a human body, and may be equal to or higher than about 0.05 Hz and equal to or lower than about 250 Hz. However, the frequency of interest is not limited thereto. The signal application unit 120 applies a signal having a frequency higher than the frequency of interest of the ECG signal to the first interface 111. For example, a frequency band higher than the frequency of interest of the ECG signal may be about 1 KHz but is not limited thereto.

Also, it would be understood by one of ordinary skill in the art that the signal applied by the signal application unit 120 may alternately use two or more frequencies higher than the frequency of interest of the biological signal.

In the drawings corresponding to the current embodiment, a ground connection refers to a reference potential that is shared with a measurement circuit unit. For example, in FIG. 1, the signal application unit 120 is grounded and this means that the signal application unit 120 shares a certain reference potential with the measurement circuit unit.

In FIG. 1, the signal application unit 120 applies an alternating current voltage (hereinafter "alternating current"), e.g., a voltage having a frequency higher than the frequency of interest of the biological signal, to the first interface 111. However, it would be understood that the current embodiment is not limited thereto and that the signal application unit 120 may apply an alternating current having a frequency higher than the frequency of interest of the biological signal directly to an internal element of the apparatus 100.

Hereinafter, it is assumed for convenience of explanation that the signal application unit 120 applies a signal having a frequency higher than the frequency of interest of the biological signal to the first interface 111. An embodiment wherein the signal application unit 120 applies an alternating current or voltage having a frequency higher than the frequency of interest of the biological signal directly to an internal element of the apparatus 100 will be described later with reference to the embodiment illustrated in detail in FIG. 6.

For example, when, the ECG signal is measured, motion artifacts may occur due to EMG generated near the interfaces 110 when the subject 200 moves, and characteristic variations of an electrical path from the skin of the subject 200 to the amplifier 150. The motion artifacts have a frequency band similar to the frequency of the ECG signal and thus may not be removed using a general filtering method.

Since the signal application unit 120 applies a signal having a frequency higher than the frequency of interest of the ECG signal to the first interface 111, the characteristic variations of the electrical path are reflected by the signal applied by the signal application unit 120, and the feedback signal generation unit 130 may generate a feedback signal for removing the motion artifacts with reference to the signal applied by the signal application unit 120.

The feedback signal generation unit 130 generates the feedback signal from component signals (hereinafter referred to as "components") generated due to the signal applied by the signal application unit 120, the feedback signal generation unit 130 generates the feedback signal using a signal obtained from at least one of the second and third interfaces 112 and 113 from among the interfaces 110. In more detail, the feedback signal generation unit 130 generates the feedback signal to be fed back to the input control unit 140 using a motion artifact signal reflected by the signal applied by the signal application unit 120. As such, the feedback signal generation unit 130 may generate the feedback signal for reducing the components generated due to the signal applied by the signal application unit 120.

As described above, the signal applied by the signal application unit 120 has a frequency higher than the frequency of interest of the biological signal and thus may be different from an original biological signal obtained from at least one of the second and third interfaces 112 and 113.

Accordingly, the feedback signal generation unit 130 extracts components having a frequency that is equal to, or similar to, the frequency of the signal applied by the signal application unit 120, from the signal obtained from at least one of the second and third interfaces 112 and 113. Motion artifacts on an electrical path from the skin of the subject 200 to the amplifier 150 are reflected in the extracted signal. As such, the feedback signal generation unit 130 may generate the feedback signal by processing the motion artifact-reflected signal, and may feed the generated feedback signal back to the input control unit 140.

In such an embodiment, the signal obtained from at least one of the second and third interfaces 112 and 113 may include at least one of a signal obtained from one of the second and third interfaces 112 and 113, a differential signal between signals obtained from the second and third interfaces 112 and 113, and an amplified signal consisting of an amplification of the differential signal. Also, the feedback signal generation unit 130 may use the signal obtained from at least one of the second and third interfaces 112 and 113, according to a selection signal 135 (as will be described in more detail with respect to FIG. 2). That is, the feedback signal generation unit 130 uses at least one of: one of the signals obtained from one of the second and third interfaces 112 and 113; the differential signal between the signals obtained from the second and third interfaces 112 and 113; and the amplified signal of the differential signal, with reference to the selection signal 135.

In one embodiment, the selection signal 135 may be input by a user. However, if a default signal is set in the apparatus 100, the selection signal 135 may be omitted.

The input control unit 140 receives the feedback signal generated by the feedback signal generation unit 130 and controls a signal input from at least one of the second and third interfaces 112 and 113 to the amplifier 150. For example, the input control unit 140 may receive the feedback signal from the feedback signal generation unit 130 to adjust an impedance of an internal element of the apparatus 100 or to apply an additional compensation signal other than signals obtained from the interfaces 110, to the internal elements of the apparatus 100. In such an embodiment, internal impedance elements of the apparatus 100 may exist in the input control unit 140 or between the interfaces 110 and input terminals of the amplifier 150.

If the input control unit 140 adjusts the impedance of the internal elements of the apparatus 100, the input control unit 140 may control the signal input from at least one of the second and third interfaces 112 and 113 to the amplifier 150, using a variable impedance element.

For example, the input control unit 140 may receive the feedback signal generated by the feedback signal generation unit 130, may adjust a real part and an imaginary part of the variable impedance element, wherein the terms "real" and "imaginary" have meanings consistent with the meanings as known to one of ordinary skill in the art, and may adjust the impedance of the apparatus 100 according to the adjustment result of the variable impedance element. As such, the input control unit 140 may reduce motion artifacts from the signal input to the amplifier 150.

An impedance element includes a real part element and an imaginary part element as described in more detail herein. A main component of the real part element is a resistance component and a main component of the imaginary part element is a reactance (capacitance and inductance) component. Also, it would be understood by one of ordinary skill in the art that a variable impedance element includes a variable resistor, a variable capacitor or other similar device, that the variable resistor may be realized by adjusting a gate voltage of a metal-oxide semiconductor ("MOS"), and that the variable capacitor may be realized as a varactor or a micro electro mechanical system ("MEMS") variable capacitor or other similar device.

Alternatively, if the input control unit 140 applies the additional compensation signal to the internal elements of the apparatus 100, the input control unit 140 allows the additional compensation signal to pass through an impedance element in the apparatus 100 which has a fixed value, and compensates for a motion artifact signal included in the signal obtained from one of the second and third interfaces 112 and 113.

The amplifier 150 amplifies the signal controlled by the input control unit 140 according to an amplification coefficient and outputs the amplified signal. Embodiments of the amplifier 150 may be, for example, an operational amplifier ("OP AMP"), but the disclosure is not limited thereto.

The LPF 160 uses the signal input from the amplifier 150 to output the biological signal to be measured. That is, the LPF 160 removes a high frequency band and then outputs a signal having a low frequency band. The signal passed through the amplifier 150 may include the signal applied by the signal application unit 120, which remains after the control of the input control unit 140, and may also include noise generated by the amplifier 150. In such an embodiment, the signal applied by the signal application unit 120 has a frequency higher than the frequency of the biological signal. Accordingly, the LPF 160 passes a signal having a frequency band lower than the frequency of the signal applied by the signal application unit 120 and filters signals having higher frequencies. As such, the signal passed through the LPF 160 is the biological signal measured from the body of the subject 200.

In one embodiment, the apparatus 100 may display the signal passed through the LPF 160 on a user interface unit (not shown) such as a monitor, or may output the signal to an external apparatus such as a display apparatus or universal serial bus ("USB") memory.

Accordingly, the apparatus 100 may output the biological signal of the body of the subject 200, from which motion artifacts are removed. In more detail, the feedback signal generation unit 130 generates the feedback signal for removing the motion artifacts, with reference to the signal applied by the signal application unit 120, and the input control unit 140 feeds back the generated feedback signal. As such, the motion artifacts included in the signal obtained from at least one of the second and third interfaces 112 and 113 may be reduced or removed and thus the output signal may more accurately reflect an actual biological signal.

Also, the elements of the apparatus 100 may correspond to one or a plurality of processors. Embodiments of a processor may be realized as an array of a plurality of logic gates, or a combination of a general-use microprocessor and memory that stores a program for controlling the microprocessor. Also, it would be understood by one of ordinary skill in the art that the elements of the apparatus 100 may be realized as other types of hardware and are not limited to the configurations discussed above.

Figure 2:
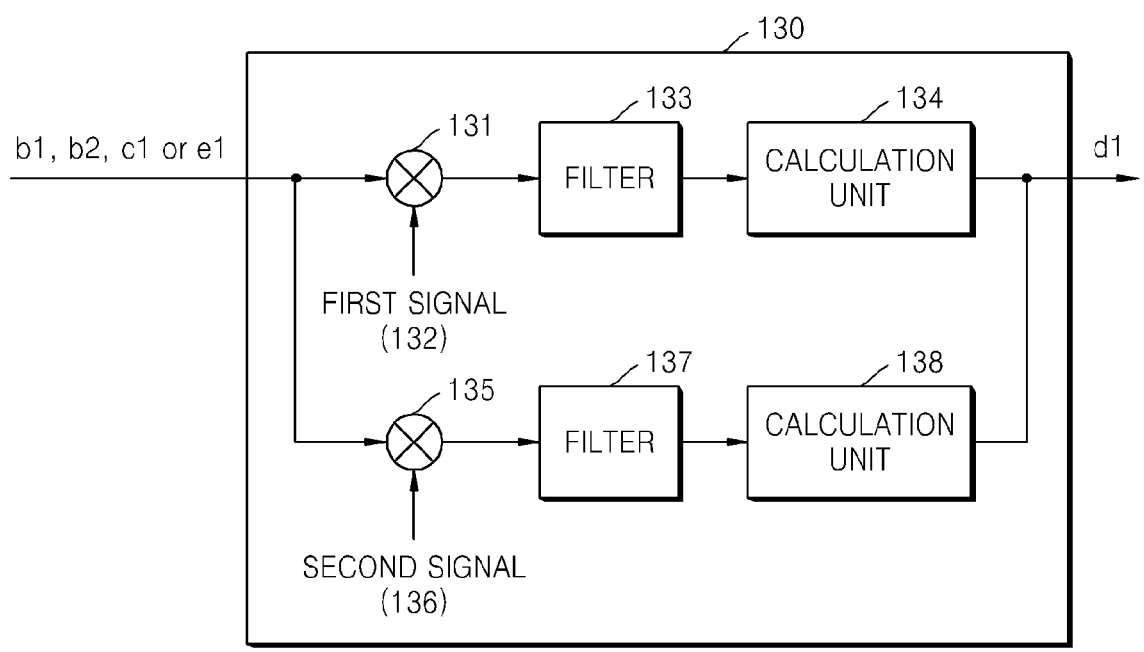
FIG. 2 is a detailed structural view of an embodiment of a feedback signal generation unit illustrated in FIG. 1 according to the present disclosure.

FIG. 2 is a detailed structural view of an embodiment of the feedback signal generation unit 130 illustrated in FIG. 1, according to the present disclosure. Referring to FIG. 2, the feedback signal generation unit 130 includes demodulators 131 and 135, filters 133 and 137, and calculation units 134 and 138.

The demodulator 131 demodulates a signal obtained from at least one of the second and third interfaces 112 and 113 using a signal applied by the signal application unit 120. The demodulator 131 may perform demodulation by multiplying the signal obtained from at least one of the second and third interfaces 112 and 113 by a first signal 132. In such an embodiment, the first signal 132 may be an in-phase signal of the signal applied by the signal application unit 120.

For example, a signal input to the demodulator 131 has a frequency band that is higher or lower than a frequency (f1) of the signal applied by the signal application unit 120, by a predetermined value (Df). Also, in one embodiment, characteristic information regarding an electrical path from the skin to the amplifier 150 is reflected to the signal input to the demodulator 131.

In such an embodiment, the signal output from the demodulator 131 has a frequency band equal to or higher than about 0 Hz and equal to or lower than about +Df, and the characteristic information regarding the electrical path from the skin to the amplifier 150 is also reflected by the signal output from the demodulator 131.

The predetermined value (Df) may be adjusted by a user or a designer of the apparatus 100. For example, if a biological signal is an ECG signal, the predetermined value (Df) may be set to be substantially the same as a frequency of interest of the ECG signal.

The filter 133 passes a frequency band of the signal demodulated by the demodulator 131, which is lower than the frequency of the signal applied by the signal application unit 120. For example, the filter 133 removes a high frequency band of the signal passed through the demodulator 131, and outputs a signal having only a low frequency band. As such, the filter 133 passes a signal having a frequency band lower than the frequency of the signal applied by the signal application unit 120 (f1).

The calculation unit 134 performs a calculation to generate a feedback signal for reducing components of the signal applied by the signal application unit 120, with reference to the signal passed through the filter 133.

For example, the calculation unit 134 generates a signal for controlling a real part of the signal input to the amplifier 150. That is, the calculation unit 134 performs a calculation to generate the feedback signal to be fed back to the input control unit 140. If the signal input to the calculation unit 134 is referred to as x, and the signal output from the calculation unit 134 is referred to as y, the calculation unit 134 may perform a calculation as represented in Equation 1.

$$y=a(x-x_0)+b \qquad \text{[Equation 1]}$$

In Equation 1, "a" represents scale adjustment, "$x_0$" represents input offset adjustment, and "b" represents output offset adjustment. In such an embodiment, a, $x_0$, and b may be previously set, e.g., set at a manufacturing facility of the apparatus 100, or may be received from a user.

The calculation unit 134 may perform the calculation as represented in Equation 1 and may generate the output signal "y" for controlling a real part of an internal impedance element of the input control unit 140. In such an embodiment, the output signal y may be a portion of the feedback signal fed back to the input control unit 140.

The demodulator 135 demodulates the signal obtained from at least one of the second and third interfaces 112 and 113. The demodulator 135 may perform demodulation by multiplying the signal obtained from at least one of the second and third interfaces 112 and 113, by a second signal 136. In such an embodiment, the second signal 136 may be an out-of-phase signal corresponding to the signal applied by the signal application unit 120. For example, the second signal 136 may be a 90°-phase-shifted signal corresponding to the signal applied by the signal application unit 120.

The filter 137 passes a frequency band of the signal demodulated by the demodulator 135, which is lower than the frequency of the signal applied by the signal application unit 120. For example, the filter 137 removes a high frequency band of the signal passed through the demodulator 135, and outputs a signal having only a low frequency band, e.g., a frequency band equal to or higher than about 0 Hz and equal to or lower than about Df.

The calculation unit 138 performs a calculation to generate a feedback signal for reducing components of the signal applied by the signal application unit 120, with reference to the signal passed through the filter 137.

For example, the calculation unit 138 generates a signal for controlling an imaginary part of the signal input to the amplifier 150. The calculation unit 138 may perform the calculation as represented in Equation 1 and may generate an output signal y for controlling an imaginary part of an internal impedance element of the input control unit 140. As described above, the output signal y may be a portion of the feedback signal fed back to the input control unit 140. One of ordinary skill in the art would recognize that the functions of the demodulators 131 and 135, the filters 133 and 137 and the calculation units 134 and 138 may be alternated, e.g., the demodulator 131 could handle the imaginary part and the demodulator 135 could handle the real part.

As illustrated in FIG. 2, when the demodulators 131 and 135 are included, each of the filters 133 and 137 may be an LPF for extracting a signal having a frequency lower than the frequency of the signal applied by the signal application unit 120, but the present disclosure is not limited thereto. That is, if the demodulators 131 and 135 are not included, each of the filters 133 and 137 may be a high pass filter ("HPF") or a band pass filter ("BPF") for passing the frequency band of the signal applied by the signal application unit 120. Accordingly, it would be understood by one of ordinary skill in the art that each of the filters 133 and 137 may be an LPF, an HPF, a BPF or the like according to whether the demodulators 131 and 135 are included or not.

Also, although the feedback control unit 130 includes one output (see dl) in FIG. 2, it would be understood by one of ordinary skill in the art that the feedback control unit 130 may include two or more outputs according to outputs of the calculation units 134 and 138.

Embodiments include configurations wherein the calculation units 134 and 138 may be realized as hardware, or may be realized as software to be processed in a digital processor after the signal is passed through an analog-digital converter ("ADC"). As such, the output of the feedback signal generation unit 130 may be a digital signal or an analog signal. Also, embodiments of the demodulators 131 and 135 may be realized as multipliers, complementary metal-oxide semiconductor ("CMOS") switches, or other similar devices.

Also, in one embodiment the feedback signal generation unit 130 may further include an amplifier or a buffer (not shown) in front of the demodulators 131 and 135 so as to amplify or buffer the signal obtained from at least one of the second and third interfaces 112 and 113.

Furthermore, in one embodiment the feedback signal generation unit 130 may further include a pre-filter (not shown) in front of the demodulators 131 and 135, so as to perform pre-filtering to pass a frequency band of the signal input to the demodulators 131 and 135 to be demodulated. For example, if the frequency of the signal applied by the signal application unit 120 is referred to as f1, and a bandwidth of a frequency to be used after performing demodulation is referred to as Df, the pre-filter included in front of the demodulators 131 and 135 may pass a signal having a frequency band equal to or higher than about (f1−Df) and equal to or lower than about (f1+Df).

Figure 3A:
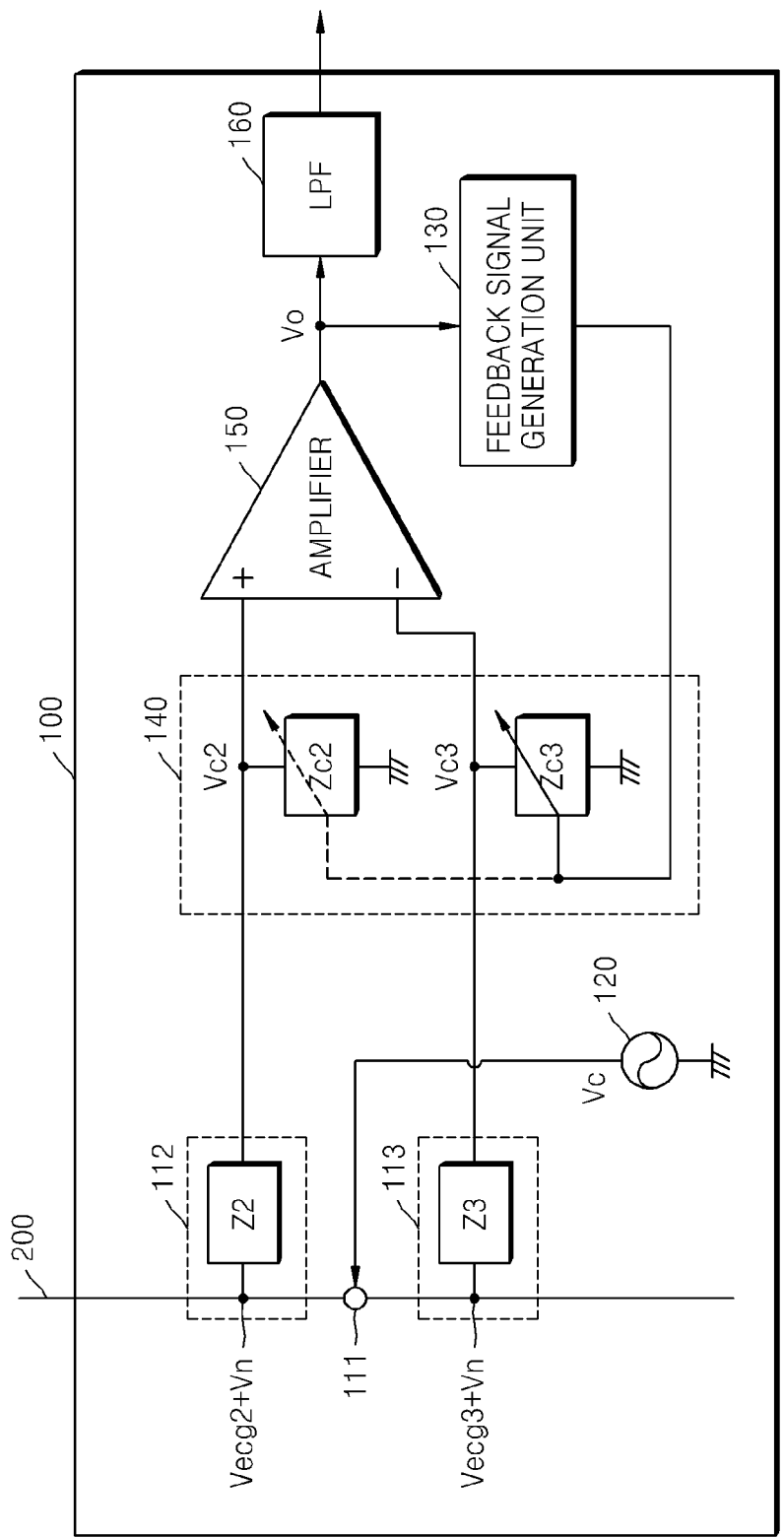
FIGS. 3A through 3C are block diagrams of the embodiment of an apparatus illustrated in FIG. 1 according to the present disclosure.
Figure 3B:
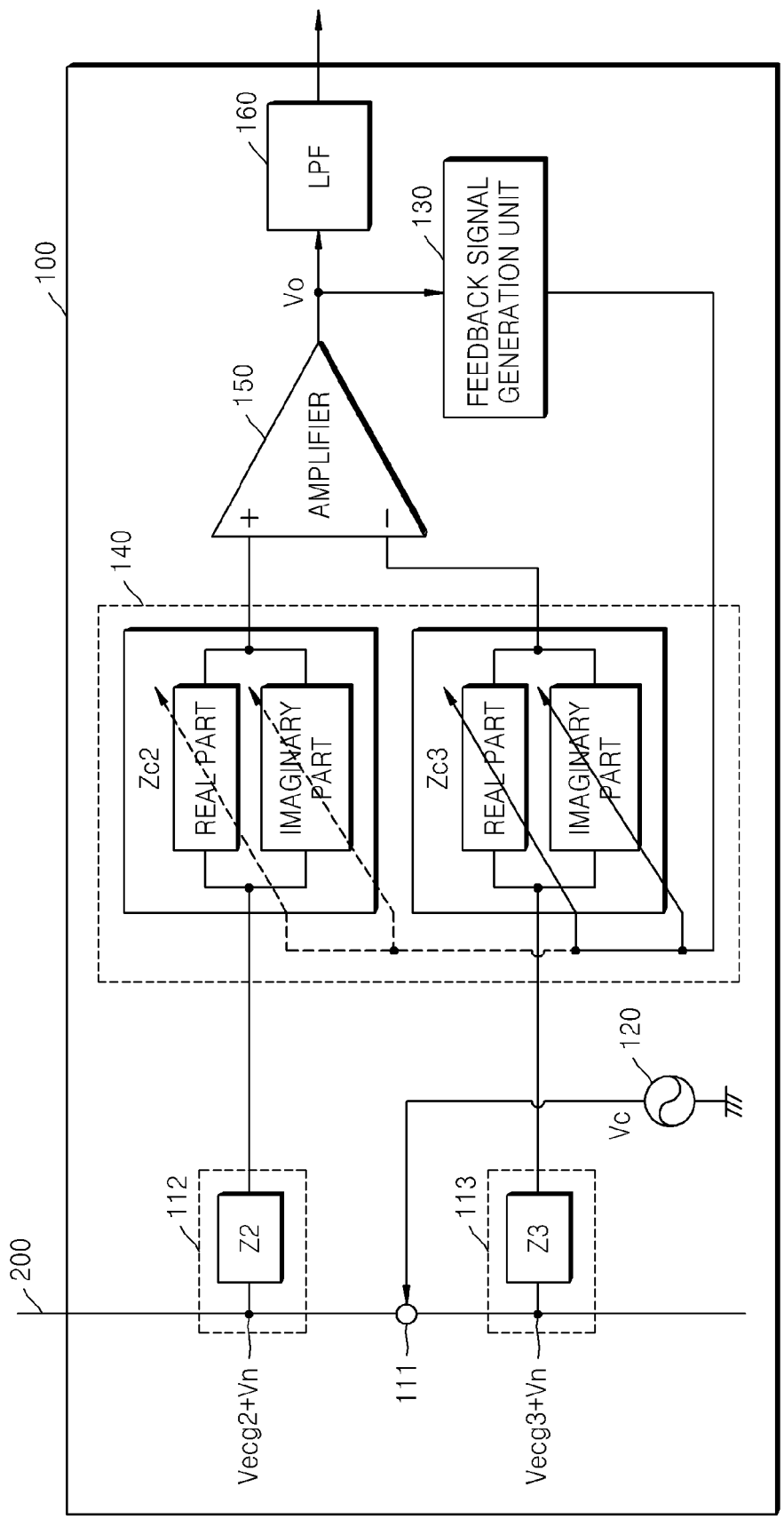
Figure 3C:
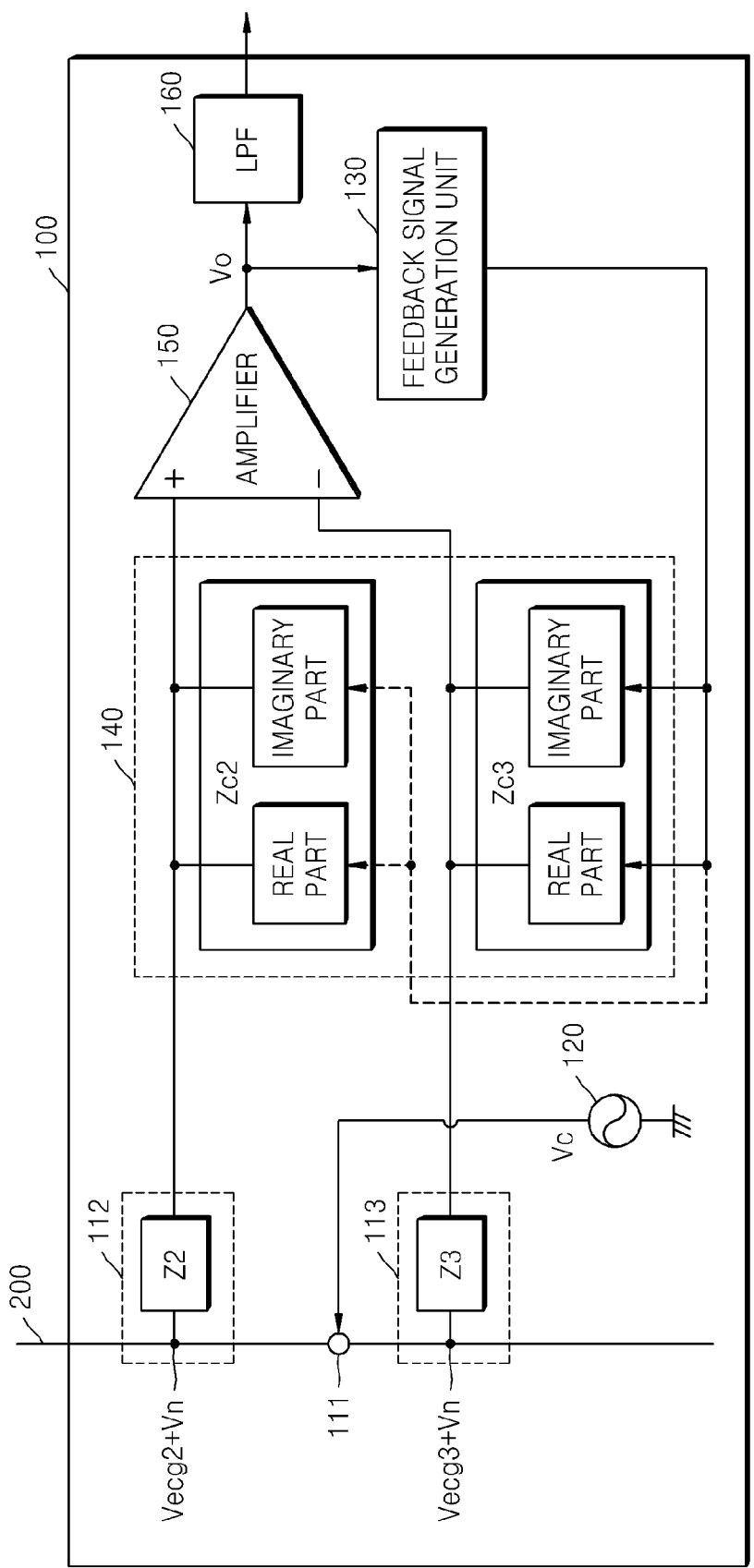

FIGS. 3A through 3C are block diagrams of the embodiment of an apparatus 100 illustrated in FIG. 1, according to an embodiment of the present disclosure. Referring to FIGS. 3A through 3C, the first through third interfaces 111 through 113 contact or are adjacent to different spots of the body, and the signal application unit 120 applies a voltage having a frequency higher than a frequency of interest of a biological signal to the first interface 111.

Hereinafter, although not particularly described for convenience of explanation, it would be understood by one of ordinary skill in the art that each signal shown in the drawings may be an alternating signal having a frequency, e.g., an alternating current, or a direct signal, e.g., a linear current. Also, hereinafter, it is assumed that a biological signal measured is an ECG signal, although, as described above, one of ordinary skill in the art would understand that alternative signals may be used.

Referring to FIGS. 3A through 3C, a voltage applied by the signal application unit 120 to the first interface 111 is referred to as Vc, an impedance of the second interface 112 is referred to as Z2, an impedance of the third interface 113 is referred to as Z3, and second and third internal impedances of the apparatus 100 are respectively referred to as Zc2 and Zc3.

Also, a signal detected by the second interface 112 includes an electrical signal Vecg2 generated from the heart of the subject 200 and a motion artifact signal Vn having a frequency similar to a frequency band of the ECG signal, and a signal detected by the third interface 113 may include an electrical signal Vecg3 generated from the heart of the subject 200 and the motion artifact signal Vn having a frequency similar to the frequency band of the ECG signal. In such an embodiment, the motion artifact signal Vn may be noise caused by movement of the subject 200, characteristic variations of an electrical path from the interfaces 110 to the skin, or characteristic variations of an electrical path from the skin of the subject 200 to an input terminal of the amplifier 150. That is, the motion artifact signal Vn is an unwanted signal that does not correspond to the ECG signal and may otherwise obscure accurate detection of the ECG signal.

Also, the motion artifact signal Vn has a frequency band similar to the frequency of the ECG signal and thus may not be removed using a general filtering method. Accordingly, the apparatus 100 removes the motion artifact signal Vn using the carrier signal Vc having a frequency higher than the frequency of the ECG signal or the motion artifact signal Vn. That is, the apparatus 100 removes the motion artifact signal Vn having a frequency close to the frequency of the ECG signal using the carrier signal Vc having a frequency higher than the frequency of the ECG signal or the motion artifact signal Vn.

Voltage signals Vc2 and Vc3 input to the amplifier 150 may be respectively defined as represented in Equations 2 and 3.

$$Vc2 = (Vecg2 + Vn + Vc)\frac{Zc2}{Z2 + Zc2} \qquad \text{[Equation 2]}$$

$$Vc3 = (Vecg3 + Vn + Vc)\frac{Zc3}{Z3 + Zc3} \qquad \text{[Equation 3]}$$

If it is assumed for convenience of explanation that the amplifier 150 has an amplification coefficient value of 1, a voltage signal Vo output from the amplifier 150 may be defined as represented in Equation 4.

$$\begin{aligned} Vo &= Vc2 - Vc3 \qquad \text{[Equation 4]} \\ &= Vecg2\frac{Zc2}{Z2 + Zc2} - Vecg3\frac{Zc3}{Z3 + Zc3} + \\ &\quad Vn\left(\frac{Zc2}{Z2 + Zc2} - \frac{Zc3}{Z3 + Zc3}\right) + \\ &\quad Vc\left(\frac{Zc2}{Z2 + Zc2} - \frac{Zc3}{Z3 + Zc3}\right) \end{aligned}$$

Referring to Equation 4, the voltage signal Vo output from the amplifier 150 includes the ECG signal, the motion artifact signal Vn of the frequency band of interest of the biological signal, and the carrier signal Vc.

For example, in FIG. 2, if a pre-filter (not shown) is included in front of the demodulators 131 and 135 of the feedback signal generation unit 130, the pre-filter performs filtering on an amplified signal of a differential signal of the second and third interfaces 112 and 113 to extract components of the carrier signal. The carrier signal has a frequency higher than the frequency of the signals Vecg2 and Vecg3 obtained from the second and third interfaces 112 and 113, and thus a filtered signal $Vo_{Filter}$ may be defined as represented in Equation 5.

$$Vo_{Filter} = Vc\left(\frac{Zc2}{Z2 + Zc2} - \frac{Zc3}{Z3 + Zc3}\right) \qquad \text{[Equation 5]}$$

Since the carrier signal has a frequency higher than the frequency of the ECG signal or a motion artifact signal of the frequency band of interest of the biological signal, the pre-filter may selectively extract a signal having the frequency of the carrier signal by performing general filtering.

As in Equation 5, the filtered signal $Vo_{Filter}$ includes electrical path characteristics reflected by the carrier signal, or imbalance information regarding electrical path characteristics from the skin to the amplifier 150.

The demodulators 131 and 135 demodulate the signal filtered by the pre-filter, using an in-phase signal and an out-of-phase signal (e.g., a 90°-phase-shifted signal) of the carrier signal, and the filters 133 and 137 perform filtering on the demodulated signal to extract components of the carrier signal.

The calculation units 134 and 136 may perform a calculation to generate a feedback signal for reducing components generated due to the voltage applied to the first interface 111, with reference to the signals output from the filters 133 and 137. That is, since the filtered signal $VO_{Filter}$ includes the imbalance information regarding electrical path characteristics from the skin to the amplifier 150, the feedback signal generation unit 130 may generate the feedback signal for reducing and minimizing the motion artifact signal Vn of the frequency band of interest of the biological signal, with reference to the imbalance information.

Referring to Equation 5, a condition for minimizing components generated due to the voltage signal applied to the first interface 111 may be defined as represented in Equation 6.

$$\frac{Zc2}{Z2+Zc2} = \frac{Zc3}{Z3+Zc3}$$ [Equation 6]

That is, the calculation units 134 and 136 perform a calculation to generate the feedback signal that satisfies the conditions of Equation 6.

The conditions of Equation 6 may be satisfied by a negative feedback of the apparatus 100. For example, in one embodiment the feedback signal generation unit 130 outputs a signal (e.g., E1) that is proportional to the filtered signal $Vo_{Filter}$ according to Equation 5. In such an embodiment, the signal that is proportional to the filtered signal $Vo_{Filter}$ according to Equation 5 may be regarded as an error caused by imbalance of electrical path characteristics at the input terminal of the amplifier 150. Thus, as the signal E1 caused by the imbalance of electrical path characteristics is fed back to the input control unit 140, the amplifier 150 is adjusted to amplify an input signal of a non-inversion input terminal or to reduce an input signal of an inversion input terminal. After that, if E1 passes through the amplifier 150, a new error may be determined as +E2 or −E2 in the feedback signal generation unit 130. A correlation between E1 and E2 may be defined as represented in Inequality 7.

$$|E2|<|E1|$$ [Inequality 7]

Accordingly, as negative feedback is repeated, an imbalance error (e.g., E1 or E2) is minimized.

The feedback signal generation unit 130 generates the feedback signal such that a ratio of the second internal impedance Zc2 for measuring the ECG signal using the second interface 112 in the apparatus 100 with respect to a sum of the second internal impedance Zc2 and the impedance Z2 of the second interface 112 is equal to a ratio of the third internal impedance Zc3 for measuring the ECG signal using the third interface 113 in the apparatus 100 with respect to a sum of the third internal impedance Zc3 and the impedance Z3 of the third interface 113.

That is, the feedback signal generation unit 130 generates the feedback signal that satisfies the condition of Equation 6, and outputs the generated feedback signal to the input control unit 140. For example, the calculation units 134 and 138 respectively calculate characteristic variations of a first electrical path from the first interface 111 to a first input terminal of the amplifier 150 through the second interface 112 and a second electrical path from the first interface 111 to a second input terminal of the amplifier 150 through the third interface 113. That is, the calculation units 134 and 138 may respectively calculate characteristic variations of the first and second electrical paths, respectively.

As such, the feedback signal generation unit 130 generates the feedback signal such that a ratio of the second internal impedance Zc2 of the apparatus 100 on the first electrical path with respect to impedance on the first electrical path is equal to a ratio of the third internal impedance Zc3 in the apparatus 100 on the second electrical path with respect to impedance on the second electrical path.

Thus, the motion artifacts of the apparatus 100 may be removed as the feedback signal generated by the feedback signal generation unit 130 is fed back, The input control unit 140 receives the feedback signal generated by the feedback signal generation unit 130 and controls the signal input from at least one of the second and third interfaces 112 and 113 to the amplifier 150.

For example, in FIG. 3A, the input control unit 140 may adjust at least one of the second and third internal impedances Zc2 and Zc3 of variable impedance elements, so as to satisfy the condition of Equation 6.

For example, in the embodiment illustrated in FIG. 3B, the input control unit 140 may adjust at least one of the second and third internal impedances Zc2 and Zc3 of the variable impedance elements, so as to satisfy the condition of Equation 6. In such an embodiment, as illustrated in FIG. 3B, each of the variable impedance elements may be divided into a real part and an imaginary part, which are arranged in series between the interfaces 110 and the amplifier 150.

Alternatively, in an alternative embodiment as illustrated in FIG. 3C, the input control unit 140 may adjust at least one of the second and third internal impedances Zc2 and Zc3 of the variable impedance elements, so as to satisfy the condition of Equation 6. In such an embodiment, as illustrated in FIG. 3C, each of the variable impedance elements may be divided into a real part and an imaginary part, which are arranged in parallel between the interfaces 110 and the amplifier 150.

As such, motion artifacts and components generated due to the signal applied to the first interface 111 are removed from the signal output from the input control unit 140. That is, the amplifier 150 receives the signal from which motion artifacts are removed, amplifies the received signal according to an amplification coefficient, and outputs the amplified signal, and the LPF 160 passes the ECG signal, i.e., a signal having only a low frequency band. As the amplified signal passes through the LPF 160, a remaining portion of the signal applied to the first interface 111 or noise added by the amplifier 150 may be removed. Accordingly, the apparatus 100 may accurately output the ECG signal of the subject 200 without motion artifacts.

As described above, motion artifacts generated when the ECG signal is measured may be efficiently removed when a signal having a frequency higher than the ECG signal is applied to the first interface 111.

That is, the input control unit 140 may remove motion artifacts of the apparatus 100 using the feedback signal received from the feedback signal generation unit 130. For example, if the input control unit 140 performs negative feedback, the impedance of internal elements of the apparatus 100 satisfies the condition of Equation 6 as a negative feedback loop is repeated, and thus a balance of impedance is obtained between the internal elements of the apparatus 100. Accordingly, motion artifacts having a frequency within the frequency band of interest of a biological signal may be efficiently removed from the ECG signal output from the apparatus 100 as a feedback procedure is repeated.

Figure 4:
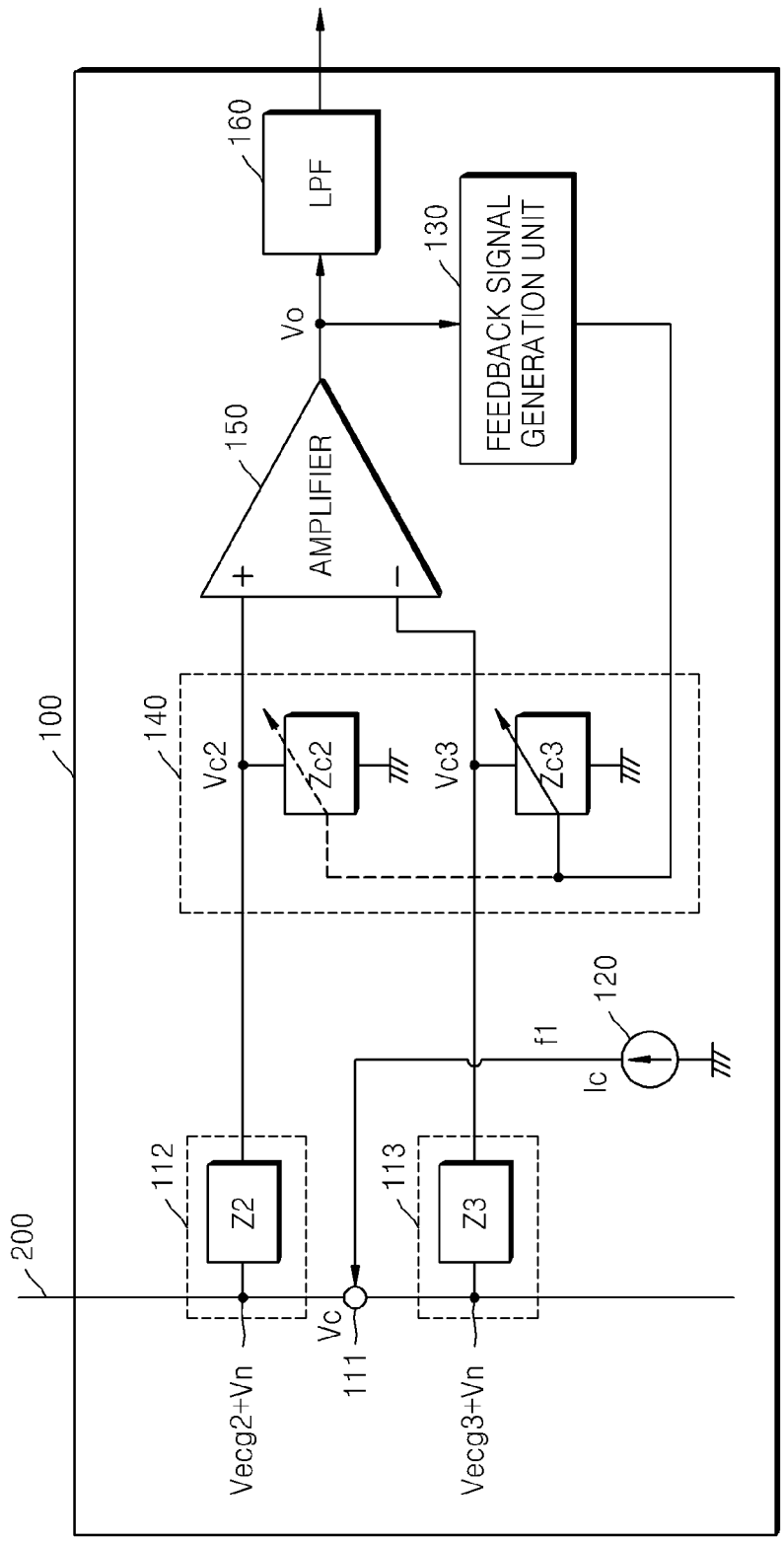
FIG. 4 is a block diagram of the embodiment of an apparatus illustrated in FIG. 1, according to the present disclosure.

FIG. 4 is a block diagram of another embodiment of the apparatus 100 illustrated in FIG. 1 according to the present disclosure. Referring to FIG. 4, the structure illustrated in FIG. 4 is substantially identical to the structure illustrated in FIG. 3A, except that the signal application unit 120 applies a current Ic having a frequency higher than a frequency of interest of a biological signal to the first interface 111, and thus a repetitive description of similar elements will be omitted.

Referring to FIG. 4, a voltage Vc generated by the first interface 111 according to the current signal Ic applied by the signal application unit 120 may be defined as represented in Equation 8.

$$Vc = \frac{Ic}{\frac{1}{Z2+Zc2} + \frac{1}{Z3+Zc3}}$$ [Equation 8]

Also, voltage signals Vc2 and Vc3 input to the amplifier 150 may be respectively defined as represented in Equations 9 and 10.

$$Vc2 = (Vecg2 + Vn + Vc)\frac{Zc2}{Z2+Zc2}$$ [Equation 9]

$$Vc3 = (Vecg3 + Vn + Vc)\frac{Zc3}{Z3+Zc3}$$ [Equation 10]

If it is assumed for convenience of explanation that the amplifier 150 has an amplification coefficient value of 1, a voltage signal Vo output from the amplifier 150 may be defined as represented in Equation 11.

$$Vo = Vc2 - Vc3$$ [Equation 11]
$$= Vecg2\frac{Zc2}{Z2+Zc2} - Vecg3\frac{Zc3}{Z3+Zc3} +$$
$$Vn\left(\frac{Zc2}{Z2+Zc2} - \frac{Zc3}{Z3+Zc3}\right) +$$
$$Vc\left(\frac{Zc2}{Z2+Zc2} - \frac{Zc3}{Z3+Zc3}\right)$$

The voltage signal Vo may also be defined as represented in Equation 12 by replacing the current signal Ic for the voltage signal Vc of Equation 11.

$$Vo = Vecg2\frac{Zc2}{Z2+Zc2} -$$ [Equation 12]
$$Vecg3\frac{Zc3}{Z3+Zc3} + Vn\left(\frac{Zc2}{Z2+Zc2} - \frac{Zc3}{Z3+Zc3}\right) +$$
$$Ic\frac{Zc2(Z3+Zc3) - Zc3(Z2+Zc2)}{Z2+Zc2+Z3+Zc3}$$

As such, the feedback signal generation unit 130 may generate a signal that satisfies a condition for reducing components generated due to the current signal Ic applied to the first interface 111, with respect to an amplified signal of a differential signal of the second and third interfaces 112 and 113.

Accordingly, the feedback signal generation unit 130 may determine the condition for removing the components generated due to a signal applied to the first interface 111, as represented in Equation 13.

$$\frac{Zc2}{Z2+Zc2} = \frac{Zc3}{Z3+Zc3}$$ [Equation 13]

Accordingly, if the condition of Equation 13 is satisfied as the apparatus 100 performs a feedback operation, the components generated due to the signal applied to the first interface 111 may be reduced and motion artifacts that exist in the frequency band of interest of the biological signal may be minimized.

Procedures similar to the subsequent procedures in the present embodiment are described above in relation to FIGS. 3A through 3C, and thus a repetitive description thereof will be omitted.

Figure 5:
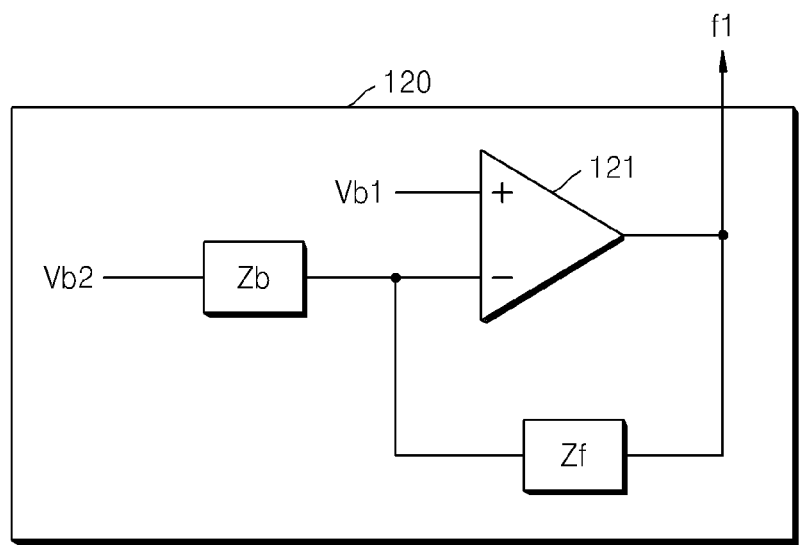
FIG. 5 is a detailed structural view of an embodiment of a signal application unit illustrated in FIG. 1 according to the present disclosure.

FIG. 5 is a detailed structural view of the signal application unit 120 illustrated in FIG. 1, according to an embodiment of the present disclosure. Referring to FIG. 5, the signal application unit 120 may include impedances Zb and Zf, and the amplifier 121. That is, as a voltage signal Vb1 is applied to a non-inversion terminal of the amplifier 121 and a voltage signal Vb2 is applied to an inversion terminal of the amplifier 121, an output of the amplifier 121 may be an alternating current. Accordingly, the apparatus 100 may apply the alternating current generated by the signal application unit 120 to the first interface 111, and may measure an ECG signal from which motion artifacts are removed.

It would be understood by one of ordinary skill in the art that the signal application unit 120 is exemplarily illustrated in FIG. 5 and thus the present disclosure is not limited to the structure illustrated in FIG. 5, and may include all elements for generating an alternating current signal or a voltage signal.

Figure 6:
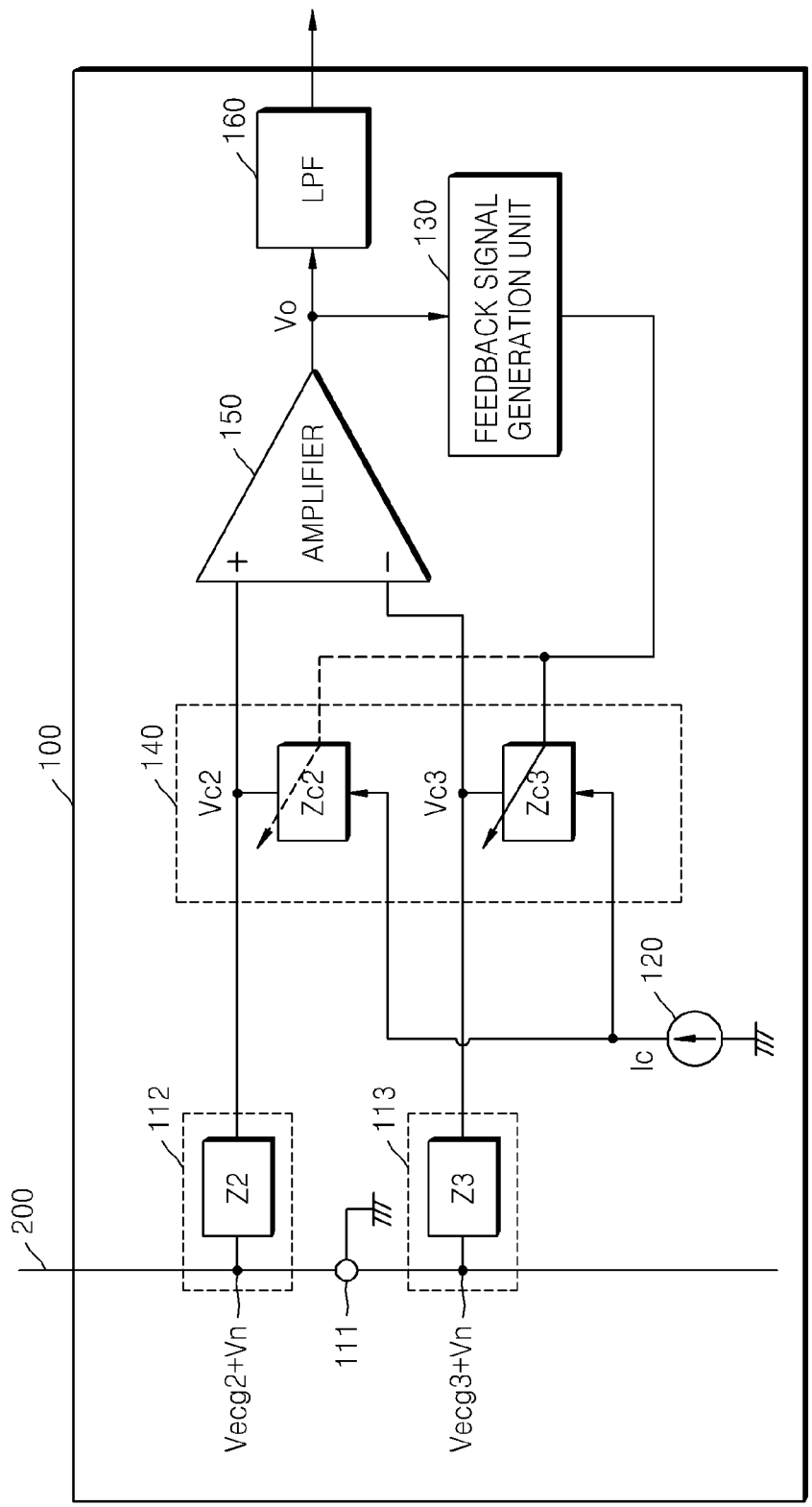
FIG. 6 is a block diagram of another embodiment of the apparatus illustrated in FIG. 1 according to the present disclosure.

FIG. 6 is a block diagram of another embodiment of the apparatus 100 illustrated in FIG. 1 according to the present disclosure. Referring to FIG. 6, the structure illustrated in FIG. 6 is substantially identical to the structure illustrated in FIG. 4, except that the signal application unit 120 applies a current signal Ic having a frequency higher than a frequency of an ECG signal directly to the second and third internal impedances Zc2 and Zc3, and that the first interface 111 is grounded, and thus a repetitive description thereof will be omitted.

That is, the input control unit 140 uses fixed impedance elements instead of the variable impedance elements. In such an embodiment, each of the fixed impedance elements may be divided into a real part and an imaginary part, and an additional compensation signal may be input to the amplifier 150 as the feedback signal generated by the feedback signal generation unit 130 passes each of the fixed impedance elements, thereby satisfying the conditions of Equation 6.

That is, in the embodiment of a structure illustrated in FIG. 6, the apparatus 100 may measure a biological signal from which motion artifacts are removed, using the method described above in relation to FIG. 4.

Figure 7:
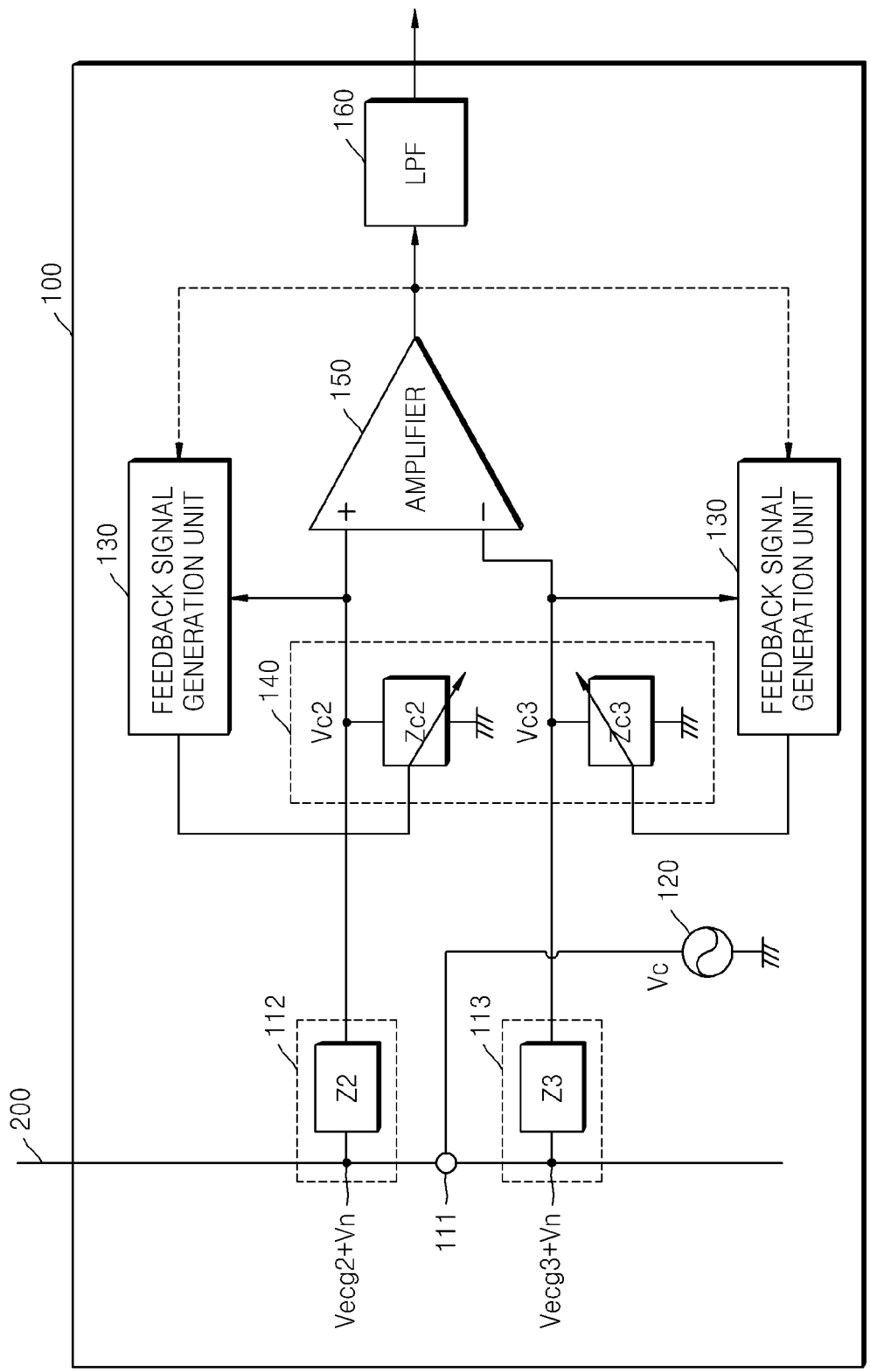
FIG. 7 is a block diagram of another embodiment of the apparatus illustrated in FIG. 1 according to the present invention.

FIG. 7 is a block diagram of another embodiment of the apparatus 100 illustrated in FIG. 1 according to the present disclosure. In the apparatus 100 illustrated in FIG. 7, two feedback signal generation units 130 separately generate feedback signals based on signals obtained from the second and third interfaces 112 and 113, and the input control unit 140 controls a signal input to the amplifier 150 using the generated feedback signals.

The operation of each of the feedback signal generation units 130 is described above in relation to FIGS. 1 through 6, and thus a repeated description thereof will not be provided here.

Also, the feedback signal generation units 130 may additionally receive an amplified differential signal, wherein the differential signals is a difference between signals obtained from the second and third interfaces 112 and 113, which is passed through the amplifier 150, and may generate the feedback signals using the amplified signal and the signals obtained from the second and third interfaces 112 and 113.

The operation of the apparatus 100 illustrated in FIG. 7 would be understood by one of ordinary skill in the art with reference to FIGS. 1 through 6, and thus a repetitive description thereof will be omitted.

Figure 8:
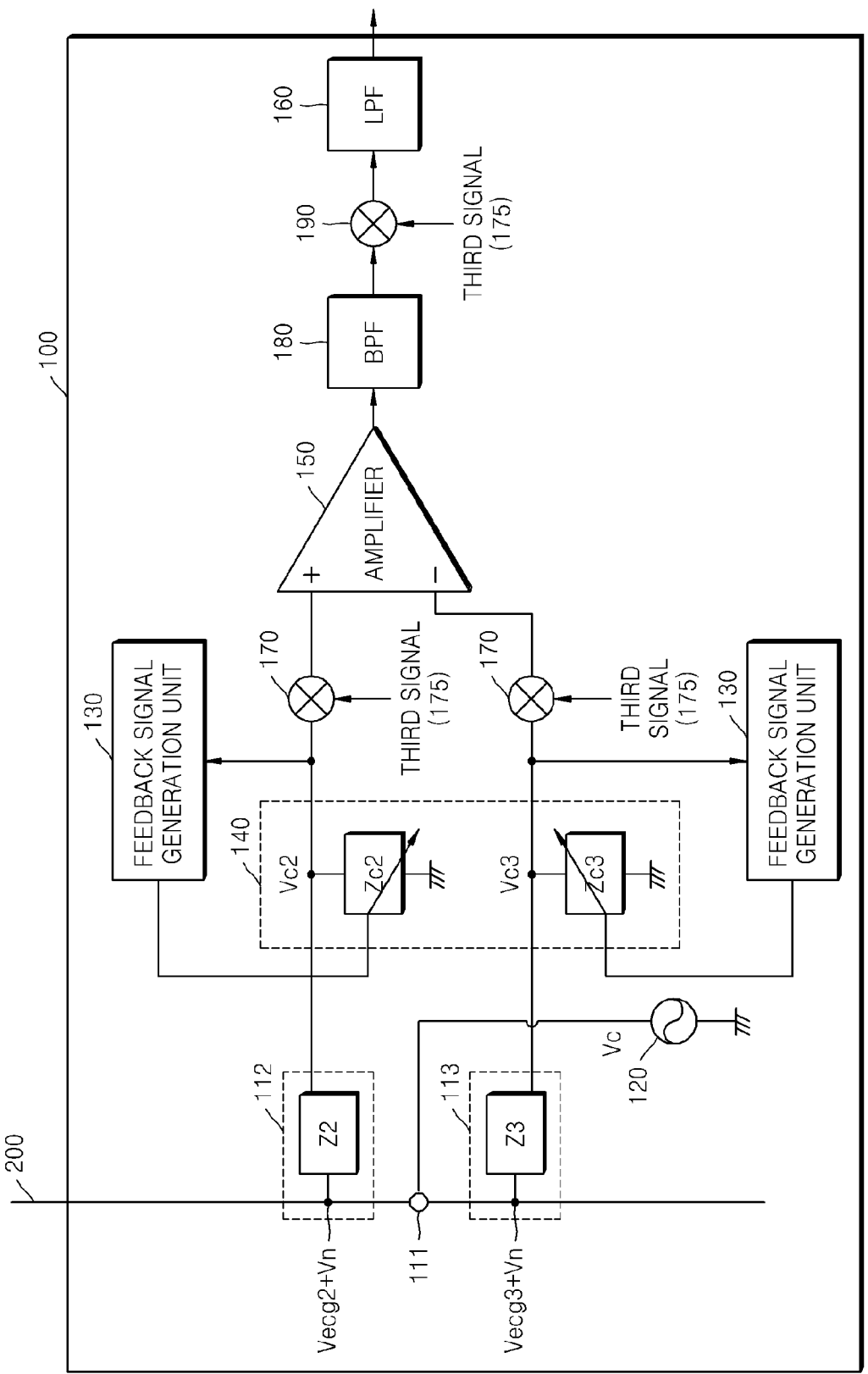
FIG. 8 is a block diagram of an embodiment of the apparatus illustrated in FIG. 1, to which modulators and a demodulator are added according to the present disclosure.

FIG. 8 is a block diagram of another embodiment of the apparatus 100 illustrated in FIG. 1 to which modulators 170 and a demodulator 190 are added, according to the present disclosure. In particular, the structure illustrated in FIG. 8 is obtained by adding the modulators 170 and the demodulator 190 to the structure illustrated in FIG. 7.

Referring to FIG. 8, the modulators 170 modulate signals obtained from the second and third interfaces 112 and 113 using a signal having a frequency higher than a frequency of a signal applied by the signal application unit 120.

In one embodiment, the modulators 170 may perform modulation by multiplying the signals obtained from the second and third interfaces 112 and 113 by a third signal 175. In such an embodiment, the third signal 175 has a frequency sufficiently higher than the frequency of the signal applied by the signal application unit 120. For example, in one embodiment the frequency of the third signal 175 may be about 4 KHz.

The amplifier 150 receives modulation signals passed through the modulators 170 and amplifies the modulation signals according to an amplification coefficient, and a BPF 180 filters a signal passed through the amplifier 150 and outputs a signal having a preset frequency band. That is, the BPF 180 performs filtering to pass a frequency band of the third signal 175, and extracts a signal modulated using the third signal 175.

The demodulator 190 demodulates the signal passed through the BPF 180 after being modulated by the modulators 170 and then being amplified by the amplifier 150. For example, the demodulator 190 may perform demodulation by multiplying the signal passed through the BPF 180 by the third signal 175.

In the apparatus 100 illustrated in FIG. 8, since modulation and demodulation are performed using an ECG signal and the third signal 175 having a frequency sufficiently higher than the frequency of the signal applied by the signal application unit 120, the signal obtained from the second interface 112 or the third interface 113 may be protected from noise generated by the amplifier 150.

Since the structure illustrated in FIG. 8 is substantially identical to the structure illustrated in FIG. 7, except that the modulators 170 and the demodulator 190 are added, the operation of the apparatus 100 illustrated in FIG. 8 would be understood by one of ordinary skill in the art with reference to FIG. 7, and thus a repetitive description thereof will be omitted.

Figure 9:
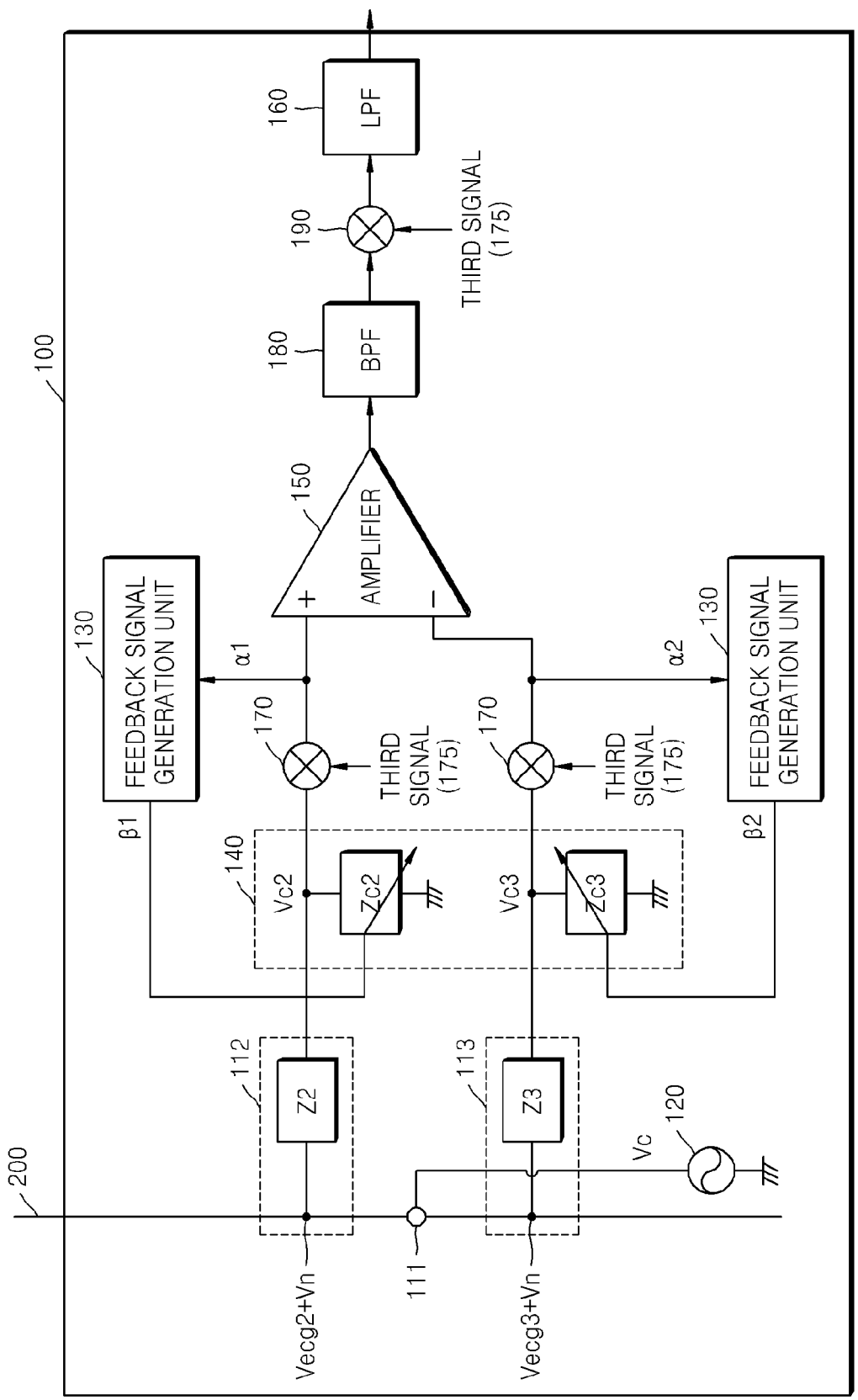
FIG. 9 is a block diagram of another embodiment of the apparatus illustrated in FIG. 1 to which modulators and a demodulator are added according to the present disclosure.

FIG. 9 is a block diagram of another embodiment of the apparatus illustrated in FIG. 1, to which modulators 170 and a demodulator 190 are added, according to the present disclosure. The structure illustrated in FIG. 9 is substantially identical to the structure illustrated in FIG. 8, except that signals passed through the modulators 170 are input to the feedback signal generation units 130, and thus a repetitive description thereof will be omitted.

The feedback signal generation units 130 generate feedback signals from components generated due to a signal applied by the signal application unit 120, using signals obtained from the second and third interfaces 112 and 113. That is, the feedback signal generation units 130 receive the signals obtained from the second and third interfaces 112 and 113 and then passed through the modulators 170, demodulate the received signals, and generate the feedback signals based on the components generated due to the signal applied by the signal application unit 120. The feedback signal generation units 130 will now be described in detail with reference to FIG. 10.

Figure 10:
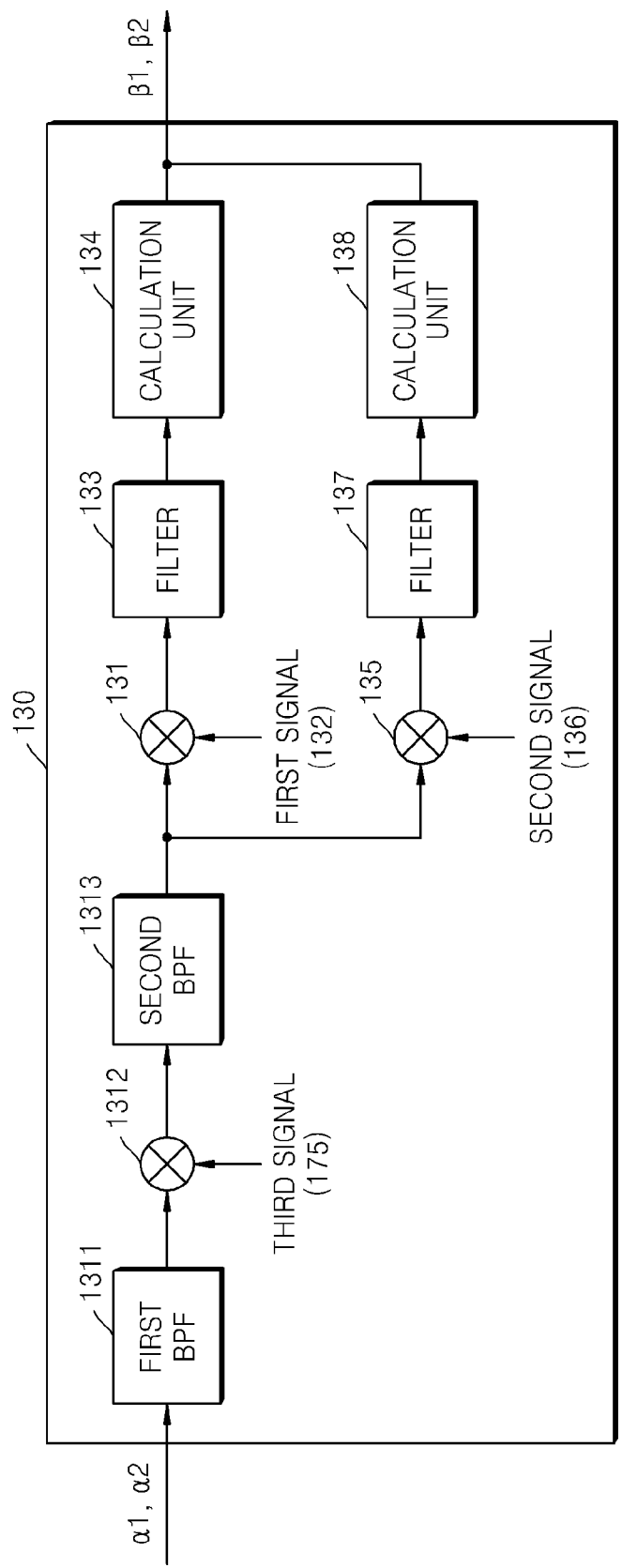
FIG. 10 is a detailed structural view of an embodiment of one of a plurality of feedback signal generation units illustrated in FIG. 9 according to the present disclosure.

FIG. 10 is a detailed structural view of an embodiment of one of the feedback signal generation units 130 illustrated in FIG. 9, according to the present disclosure. Referring to FIG. 10, the feedback signal generation unit 130 is substantially identical to the feedback signal generation unit 130 illustrated in FIG. 2, except that a first BPF 1311, a demodulator 1312, and a second BPF 1313 are added, and thus a repetitive description thereof will be omitted.

The first BPF 1311 performs band-pass filtering on a signal passed through the modulator 170 and passes a frequency band of a signal used by the modulator 170. That is, the first BPF 1311 outputs a signal of a frequency band of the third signal 175. As such, the signal passed through the first BPF 1311 includes the third signal 175 and a signal obtained from the second interface 112 or the third interface 113 and then is modulated by the modulator 170.

The demodulator 1312 demodulates the signal passed through the first BPF 1311 using the signal used by the modulator 170. That is, the demodulator 1312 may perform demodulation by multiplying the signal passed through the first BPF 1311, by the third signal 175. As such, the signal passed through the demodulator 1312 is a signal related to the third signal 175.

The second BPF 1313 performs band-pass filtering on the signal passed through the demodulator 1312 and passes a frequency band of a signal applied by the signal application unit 120. That is, the second BPF 1313 extracts a signal of the frequency band of the signal applied by the signal application unit 120.

Accordingly, since the signal obtained from the second interface 112 or the third interface 113 is modulated and demodulated using the third signal 175 the signal output from the second BPF 1313 is the signal obtained from the second interface 112 or the third interface 113.

A subsequent procedure to be performed by the demodulators 131 and 135, the filters 133 and 137, and the calculation units 134 and 138 as is described above in relation to FIG. 2, and thus a repetitive description thereof will be omitted.

Figure 11:
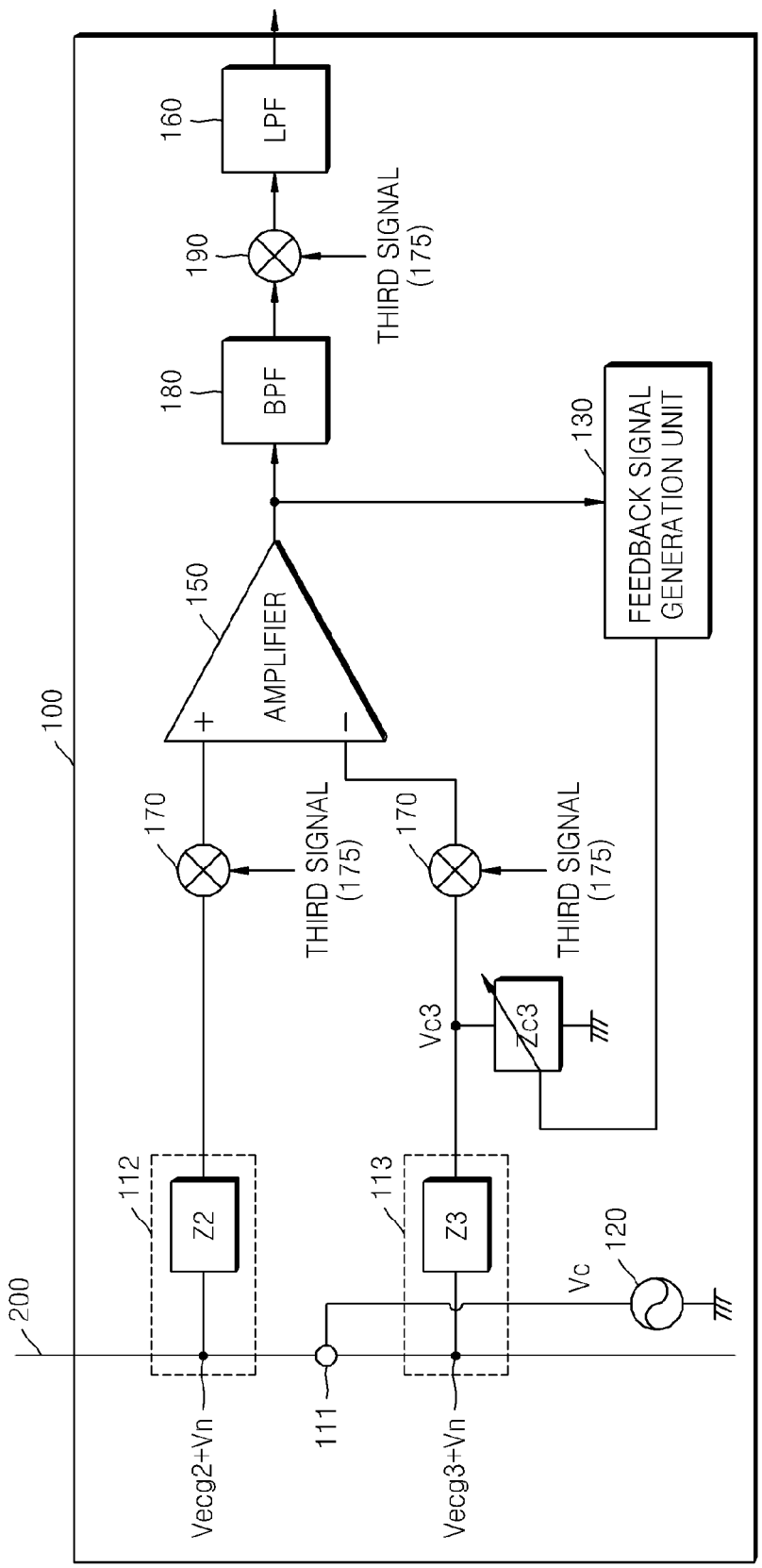
FIG. 11 is a block diagram of another embodiment of the apparatus illustrated in FIG. 1 to which modulators and a demodulator are added according to the present disclosure.

FIG. 11 is a block diagram of another embodiment of the apparatus 100 illustrated in FIG. 1, to which modulators 170 and a demodulator 190 are added, according to the present disclosure. The structure illustrated in FIG. 11 is substantially identical to the structure illustrated in FIG. 9, except that the input control unit 140 adjusts a third internal impedance Zc3 by performing negative feedback, and that the feedback signal generation unit 130 receives an amplified signal of a differential signal between modulation signals of signals obtained from the second and third interfaces 112 and 113, and thus a repetitive description thereof will be omitted.

The operation of the apparatus 100 illustrated in FIG. 11 would be understood by one of ordinary skill in the art with reference to FIGS. 1 through 3, 9 and 10, and thus a repetitive description thereof will be omitted.

Figure 12:
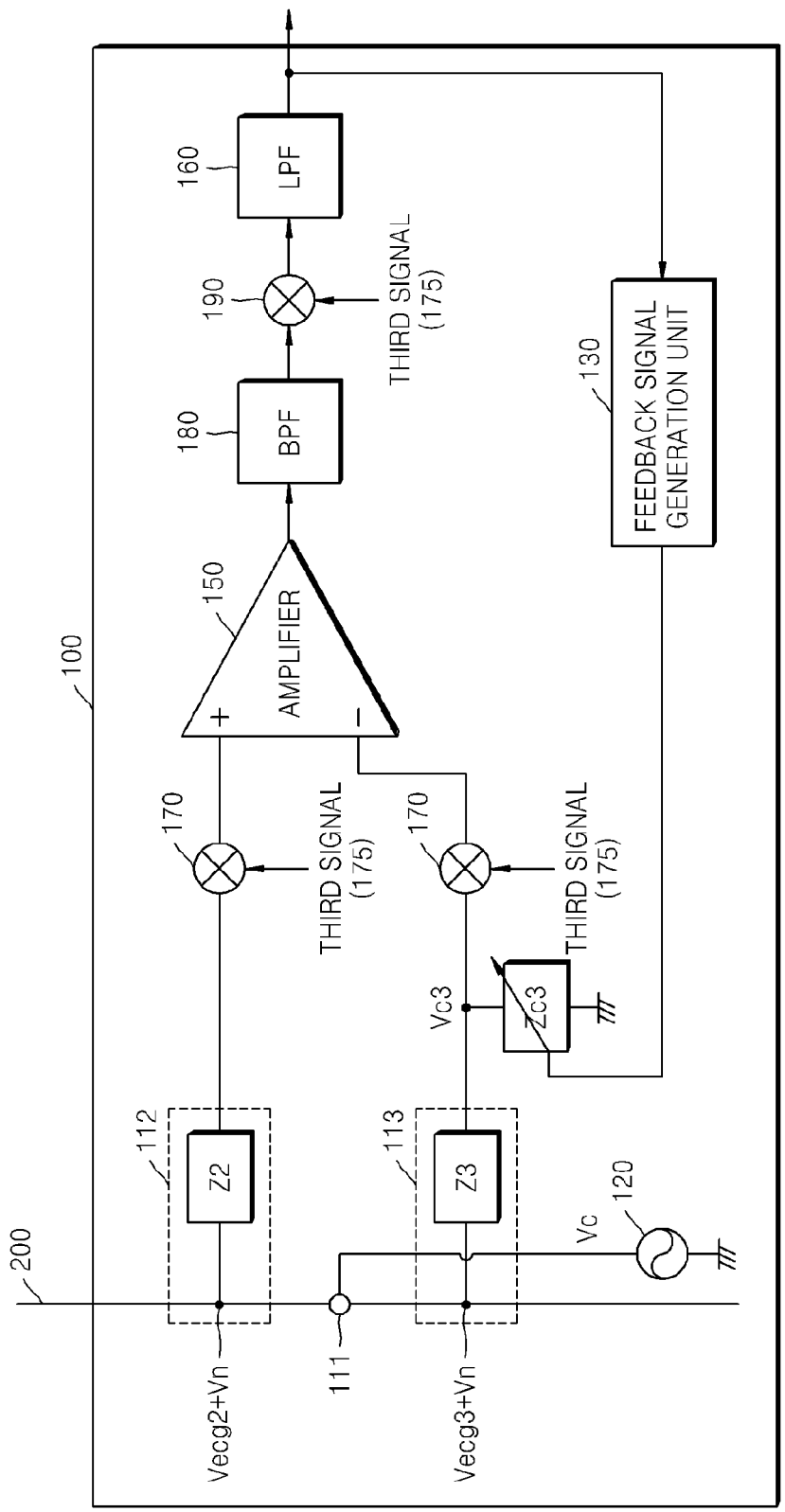
FIG. 12 is a block diagram of another embodiment of the apparatus illustrated in FIG. 1 to which modulators and a demodulator are added according to the present disclosure.
Figure 13:
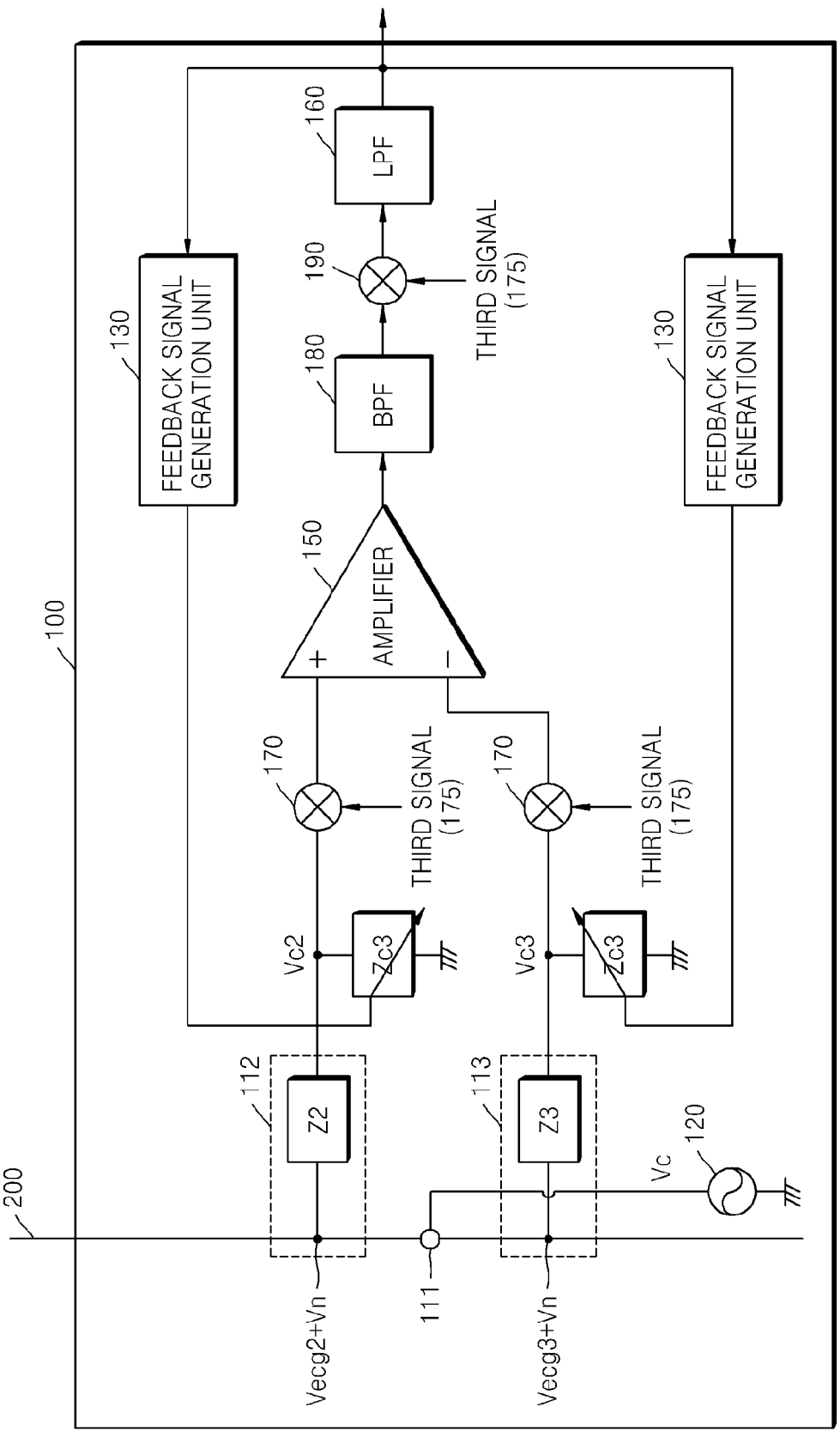
FIG. 13 is a block diagram of another embodiment of the apparatus illustrated in FIG. 1 to which modulators and a demodulator are added according to the present disclosure.

FIG. 12 is a block diagram of another embodiment of the apparatus 100 illustrated in FIG. 1, to which modulators 170 and a demodulator 190 are added, according to the present disclosure. FIG. 13 is a block diagram of another embodiment of the apparatus 100 illustrated in FIG. 1, to which modulators 170 and a demodulator 190 are added, according to the present disclosure. In the apparatus 100 illustrated in FIGS. 12 and 13, the feedback signal generation unit 130 receives a signal passed through the LPF 160. In such an embodiment, the apparatus 100 illustrated in FIGS. 12 *and* 13 uses the feedback signal generation unit 130 illustrated in FIG. 2.

The operation of the apparatus 100 illustrated in FIG. 12 or 13 would be understood by one of ordinary skill in the art with reference to FIGS. 8, 9, and 11, and thus a repetitive description thereof will be omitted.

A carrier signal having a frequency higher than a frequency of interest of a biological signal may be mixed with another component signal in a signal applied by the signal application unit 120 to the first interface 111. In such an embodiment, the other component signal may be a direct current ("DC") bias for giving an offset to a frequency (e.g., f1) of the carrier signal, or a fadd signal having a frequency lower than the frequency of the carrier signal. According to the current embodiment, the fadd signal may be a feedback signal generated by the feedback signal generation unit 130.

For example, in the signal applied by the signal application unit 120, a reference DC bias, components of a low frequency alternating signal having a frequency equal to or higher than about 0.5 Hz, which are input from the feedback signal generation unit 130, and equal to or lower than about 250 Hz, and components of a high frequency carrier signal having a frequency of about 1 KHz, are all mixed.

Figure 14:
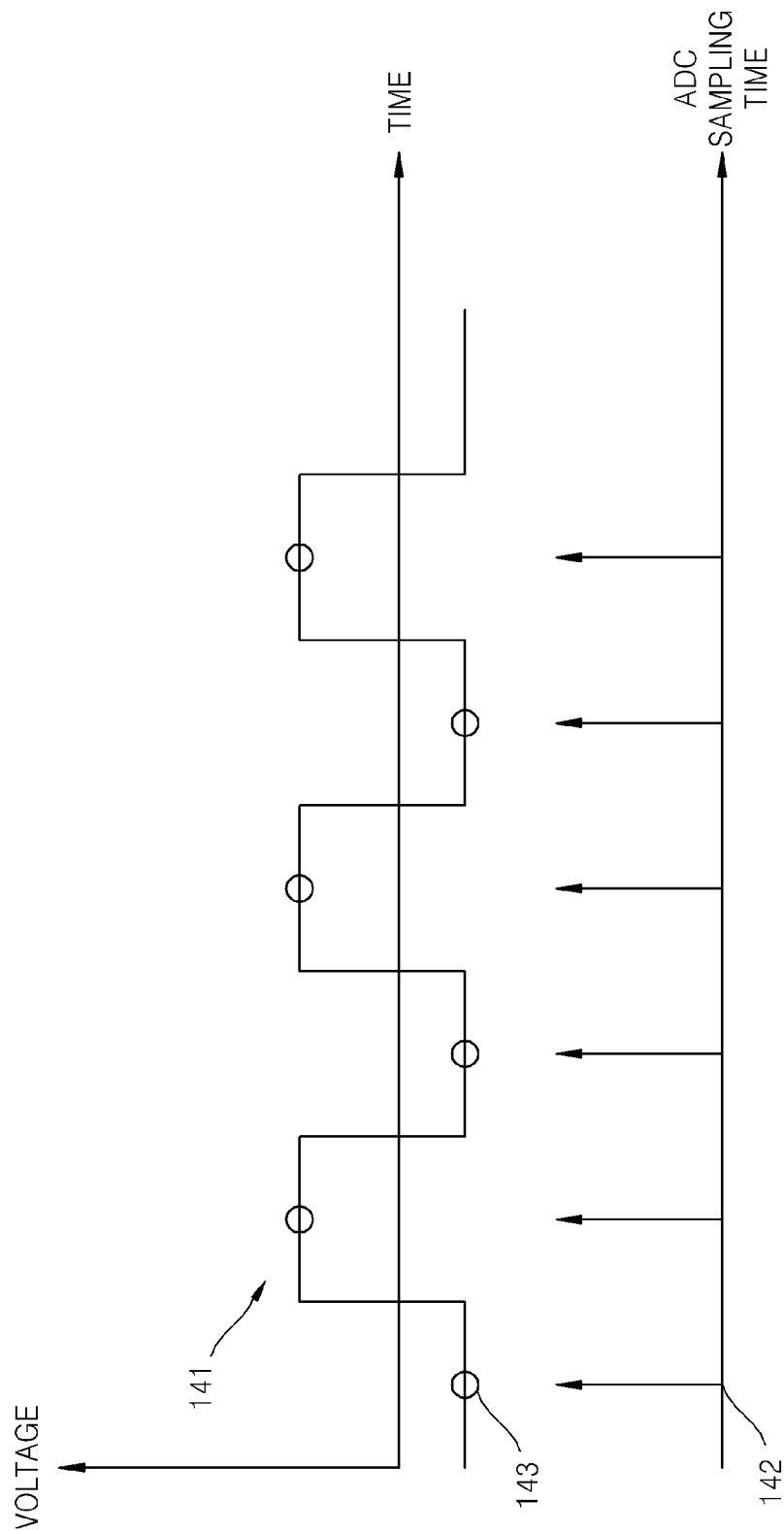
FIG. 14 is a graph illustrating an embodiment of a method of realizing a demodulator illustrated in FIGS. 2, 8, 9, 11, 12 and 13, as an analog-digital converter ("ADC"), according to the present disclosure.

FIG. 14 is a graph illustrating an embodiment of a method of realizing the demodulator 131 or 135 illustrated in FIG. 2, or the demodulator 190 illustrated in FIGS. 8, 9, 11, 12 and 13, as an ADC, according to the present disclosure. The demodulator 131, 135, or 190 may be realized by using the ADC as illustrated in FIG. 14.

Referring to FIG. 14, a modulation signal 141 may be sampled using a sampling signal 142 so as to obtain sampled values 143, and the sampled values 143 may be extremely identical to values of a signal passed through the demodulator 131, 135, or 190. In such an embodiment, if the modulation signal 141 has a frequency f, the sampling signal 142 may be generated in cycle of $1/(2f)$.

Accordingly, the demodulator 131, 135, or 190 of the apparatus 100 may be realized with software by using an ADC.

Figure 15:
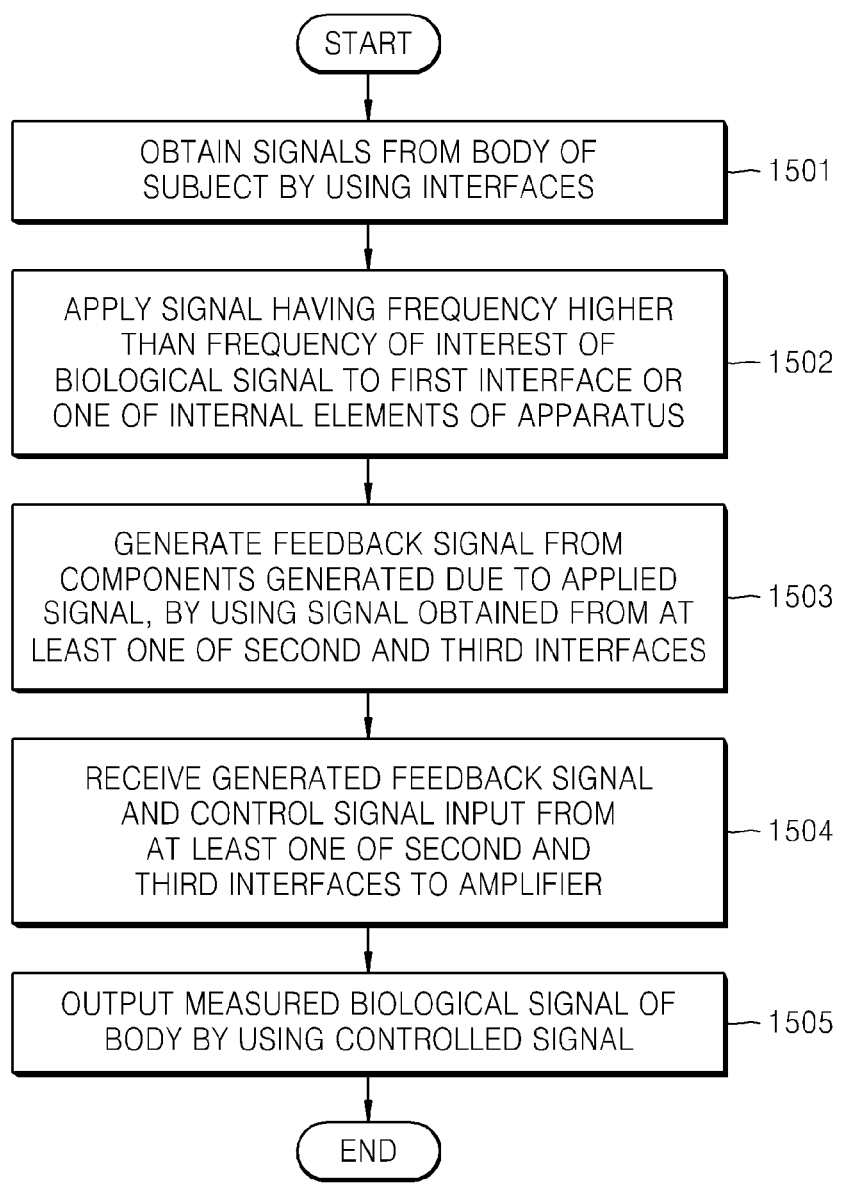
FIG. 15 is a flowchart of an embodiment of a method of measuring a biological signal according to the present disclosure.

FIG. 15 is a flowchart of a method of measuring a biological signal, according to an embodiment of the present disclosure. Referring to FIG. 15, the method according to the current embodiment includes operations performed sequentially by the apparatus 100 illustrated in FIG. 1. Accordingly, descriptions made above in relation to the apparatus 100 may also be applied to the method according to the current embodiment and may not be provided here.

In operation 1501, signals are obtained from the body of the subject 200 using three or more interfaces 110. In such an embodiment, the interfaces 110 contact or are adjacent to the body of the subject 200.

In operation 1502, the signal application unit 120 applies a signal having a frequency higher than a frequency of interest of a biological signal to the first interface 111 or one of the internal elements of the apparatus 100. In such an embodiment, the signal applied by the signal application unit 120 may be an alternating voltage or current having a frequency higher than the frequency of interest of the biological signal.

In operation 1503, the feedback signal generation unit 130 generates a feedback signal from components generated due to the signal applied by the signal application unit 120, using a signal obtained from at least one of the second and third interfaces 112 and 113.

In operation 1504, the input control unit 140 receives the feedback signal generated by the feedback signal generation unit 130 and controls a signal input from at least one of the second and third interfaces 112 and 113 to the amplifier 150. In such an embodiment, the input control unit 140 may control the signal input to the amplifier 150 by adjusting the impedance of an internal element of the apparatus 100 using a variable impedance element, or by applying an additional signal to the internal element of the apparatus 100.

In operation 1505, the LPF 160 outputs a measured biological signal of the body using the signal controlled by the input control unit 140.

As the above feedback procedure is repeated, the apparatus 100 may measure a biological signal from which motion artifacts generated due to movement of the subject 200, or the like, are removed.

As described above, according to one or more of the above embodiments of the present disclosure, a biological signal from which motion artifacts generated due to movement of a subject are removed may be measured. Also, a biological signal from which noise generated by an amplifier for amplifying a signal detected from a subject is removed may be measured.

Meanwhile, one or more of the above embodiments of the present disclosure can be written as computer programs and can be implemented in general-use digital computers that execute the programs using a computer readable recording medium. Also, the data structure used in the embodiments of the present disclosure described above can be recorded on a computer readable recording medium via various means. Examples of the computer readable recording medium include magnetic storage media (e.g., ROM, floppy disks, hard disks, etc.), optical recording media (e.g., CD-ROMs, or DVDs), etc.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. An apparatus for measuring a biological signal of a body, the apparatus comprising:
   at least three interfaces;
   a signal application unit which applies a signal having a predetermined frequency which is higher than a frequency of interest of the biological signal directly to a first interface from among the at least three interfaces, and one of a plurality of internal elements of the apparatus;
   a feedback signal generation unit which extracts component signals from a signal obtained from the body using at least one of a second interface and a third interface from among the at least three interfaces and generates a feedback signal for removing motion artifacts based on the extracted component signals wherein the feedback signal generation unit comprises a demodulator which demodulates the signal obtained from at least one of the second interface and the third interface using the signal applied by the signal application unit; and
   an input control unit which receives the generated feedback signal and controls a signal input from at least one of the second interface and third interface to an amplifier to remove the motion artifacts included in the input signal by using the feedback signal,
   wherein a difference between a frequency of each of the component signals and the frequency of the applied signal is within a predetermined range.

2. The apparatus of claim 1, wherein the feedback signal generation unit generates the feedback signal which reduces the component signals generated due to the signal applied by the signal application unit.

3. The apparatus of claim 1, wherein the feedback signal generation unit comprises:

a filter which passes a frequency band of the demodulated signal and generates a filtered signal using the signal applied by the signal application unit; and a calculation unit which performs a calculation to generate the feedback signal which reduces the component signals generated due to the signal applied by the signal application unit, with respect to the filtered signal.

4. The apparatus of claim 1, wherein the demodulator performs demodulation using an in-phase signal and an out-of-phase signal with respect to the signal applied by the signal application unit.

5. The apparatus of claim 1, wherein the feedback signal generation unit comprises a calculation unit which calculates characteristic variations of a first electrical path from the first interface to the amplifier through the second interface, and a second electrical path from the first interface to the amplifier through the third interface.

6. The apparatus of claim 5, wherein the feedback signal generation unit generates the feedback signal such that a ratio of a second internal impedance in the apparatus on the first electrical path with respect to an impedance on the first electrical path is substantially equal to a ratio of a third internal impedance in the apparatus on the second electrical path with respect to an impedance on the second electrical path.

7. The apparatus of claim 1, wherein the input control unit controls the signal input to the amplifier by at least one of adjusting an impedance of an internal element of the apparatus using a variable impedance element, and applying an additional signal to the internal element of the apparatus.

8. The apparatus of claim 1, further comprising:
a modulator which modulates the signal obtained from at least one of the second interface and the third interface and generates a modulated signal using a signal having a frequency higher than the frequency of the signal applied by the signal application unit;
an amplifier which receives and amplifies the modulated signal and generates an amplified signal; and
a demodulator which demodulates the amplified signal using a signal used by the modulator.

9. The apparatus of claim 1, wherein the demodulator comprises an analog-digital converter.

10. A method of measuring a biological signal of a body using an apparatus for measuring the biological signal, the method comprising:
applying a signal having a predetermined frequency higher than a frequency of interest of the biological signal directly to a first interface from among the at least three interfaces and one of a plurality of internal elements of the apparatus;
extracting component signals from a signal obtained from the body using at least one of a second interface and a third interface from among the at least three interfaces;
generating a feedback signal for removing motion artifacts based on the extracted component signals wherein the generating of the feedback signal comprises demodulating the signal obtained from at least one of the second interface and the third interface using the applied signal;
receiving the generated feedback signal, controlling a signal input from at least one of the second interface and the third interface to remove the motion artifacts included in the input signal by using the feedback signal and sending the controlled signal to an amplifier; and
outputting a measured biological signal of the body using the controlled signal,
wherein a difference between a frequency of each of the component signals and the frequency of the applied signal is within a predetermined range.

11. The method of claim 10, wherein the generating of the feedback signal comprises generating the feedback signal which reduces the component signals generated due to the applied signal.

12. The method of claim 10, wherein the generating of the feedback signal comprises:
passing a frequency band of the demodulated signal to generate a filtered signal; and
performing a calculation to generate the feedback signal which reduces the component signals generated due to the applied signal, with respect to the filtered signal.

13. The method of claim 12, wherein the generating of the feedback signal comprises:
passing a frequency band of the demodulated signal, which is lower than the frequency of the applied signal, to generate a filtered signal; and
performing a calculation to generate the feedback signal, with respect to the filtered signal.

14. The method of claim 10, wherein the controlling of the signal comprises adjusting an impedance of an internal element of the apparatus by at least one of using a variable impedance element, and applying an additional signal to the internal element of the apparatus.

15. A non-transitory computer readable recording medium having recorded thereon a computer program for executing the method of claim 10.

16. An apparatus for measuring a biological signal of a body, the apparatus comprising:
at least three interfaces;
a signal application unit which applies a carrier signal which has a predetermined frequency higher than a frequency of interest of the biological signal directly to a first interface from among the at least three interfaces, and one of a plurality of internal elements of the apparatus; and
a feedback signal generation unit which generates a feedback signal from component signals generated due to the applied carrier signal, using a signal obtained from the body using at least one of a second interface and a third interface from among the at least three interfaces wherein the feedback signal generation unit comprises a demodulator which demodulates the signal obtained from at least one of the second interface and the third interface using the signal applied by the signal application unit,
wherein the carrier signal is synthesized based on a signal having a frequency higher than a frequency of interest of the biological signal, and the feedback signal received from the feedback signal generation unit, and is output from the signal application unit.

* * * * *